United States Patent
Anton et al.

(10) Patent No.: US 10,011,837 B2
(45) Date of Patent: Jul. 3, 2018

(54) SIRNAS AND THEIR USE IN METHODS AND COMPOSITIONS FOR THE TREATMENT AND/OR PREVENTION OF EYE CONDITIONS

(71) Applicant: Sylentis SAU, Madrid (ES)

(72) Inventors: Ana Isabel Jimenez Anton, Madrid (ES); Victoria Gonzalez Fajardo, Madrid (ES); Veronica Ruz Palomar, Madrid (ES)

(73) Assignee: SYLENTIS SAU, Madrid (ES)

( * ) Notice: Subject to any disclaimer, the term of this patent is extended or adjusted under 35 U.S.C. 154(b) by 0 days.

(21) Appl. No.: 15/123,298

(22) PCT Filed: Mar. 4, 2015

(86) PCT No.: PCT/EP2015/054521
§ 371 (c)(1),
(2) Date: Sep. 2, 2016

(87) PCT Pub. No.: WO2015/132303
PCT Pub. Date: Sep. 11, 2015

(65) Prior Publication Data
US 2017/0058279 A1    Mar. 2, 2017

Related U.S. Application Data

(60) Provisional application No. 61/947,614, filed on Mar. 4, 2014.

(51) Int. Cl.
*A61K 48/00*    (2006.01)
*C07H 21/02*    (2006.01)
(Continued)

(52) U.S. Cl.
CPC ........ *C12N 15/1138* (2013.01); *A61K 9/0048* (2013.01); *A61K 31/7088* (2013.01);
(Continued)

(58) Field of Classification Search
CPC ............ C12N 15/1138; C12N 2310/14; A61K 31/7088
(Continued)

(56) References Cited

U.S. PATENT DOCUMENTS 4,343,794 A    8/1982 Podos et al.
4,617,299 A    10/1986 Knepper
(Continued)

FOREIGN PATENT DOCUMENTS

AU    2005276245    3/2006
EP    1 527 176    1/2007
(Continued)

OTHER PUBLICATIONS

Abrams et al., "Comparison of Three Tonometers for Measuring Intraocular Pressure in Rabbits," Invest Ophthalmol Vis Sci. Apr. 1996, 37(5):940-944.
(Continued)

*Primary Examiner* — Terra C Gibbs
(74) *Attorney, Agent, or Firm* — Margaret B. Brivanlou; Kenneth H. Sonnenfeld; King & Spalding LLP

(57) ABSTRACT

The present invention relates to methods, compositions and dosages that decrease IOP of the eye, comprising a 19 nucleotide double-stranded RNA molecule.

11 Claims, 4 Drawing Sheets

(51) Int. Cl.
  *C07H 21/04* (2006.01)
  *C12N 15/11* (2006.01)
  *C12N 15/113* (2010.01)
  *A61K 31/713* (2006.01)
  *A61K 9/00* (2006.01)
  *A61K 31/7088* (2006.01)

(52) U.S. Cl.
  CPC ........ *A61K 31/713* (2013.01); *C12N 2310/14* (2013.01); *C12N 2320/35* (2013.01)

(58) Field of Classification Search
  USPC .......................................... 514/44; 536/24.5
  See application file for complete search history.

(56) References Cited

U.S. PATENT DOCUMENTS

| | | |
|---|---|---|
| 4,652,586 A | 3/1987 | Nathanson |
| 4,757,089 A | 7/1988 | Epstein |
| 4,812,448 A | 3/1989 | Knepper |
| 5,075,323 A | 12/1991 | Fain et al. |
| 5,242,943 A | 9/1993 | Louis et al. |
| 5,260,059 A | 11/1993 | Acott et al. |
| 5,464,866 A | 11/1995 | Clark et al. |
| 5,545,626 A | 8/1996 | Stein et al. |
| 5,585,401 A | 12/1996 | Brandt et al. |
| 6,365,576 B1 | 4/2002 | Carr |
| 6,372,249 B1 | 4/2002 | Smith et al. |
| 6,489,307 B1 | 12/2002 | Phillips et al. |
| 7,176,304 B2 | 2/2007 | McSwiggen et al. |
| 7,294,504 B1 | 11/2007 | Wang |
| 7,462,602 B2 | 12/2008 | Schultz et al. |
| 7,521,431 B2 | 4/2009 | Reich et al. |
| 7,579,457 B2 | 8/2009 | Khvorova et al. |
| 7,592,324 B2 | 9/2009 | Shepard et al. |
| 7,592,325 B2 | 9/2009 | Jimenez et al. |
| 7,618,814 B2 | 11/2009 | Bentwich |
| 7,655,789 B2 | 2/2010 | Khvorova et al. |
| 7,687,665 B2 | 3/2010 | Yao et al. |
| 7,691,997 B2 | 4/2010 | Khvorova et al. |
| 7,700,575 B2 | 4/2010 | Andrew et al. |
| 8,030,284 B2 | 10/2011 | Jimenez et al. |
| 8,090,542 B2 | 1/2012 | Khvorova et al. |
| 2002/0055536 A1 | 5/2002 | DeWitte et al. |
| 2002/0114784 A1 | 8/2002 | Li et al. |
| 2002/0165158 A1 | 11/2002 | King |
| 2004/0029275 A1 | 2/2004 | Brown et al. |
| 2004/0115641 A1 | 6/2004 | Cowsert et al. |
| 2004/0167090 A1 | 8/2004 | Monahan et al. |
| 2004/0198640 A1 | 10/2004 | Leake et al. |
| 2004/0209832 A1 | 10/2004 | McSwiggen et al. |
| 2004/0224405 A1 | 11/2004 | Leake et al. |
| 2004/0235031 A1 | 11/2004 | Schultz et al. |
| 2004/0259247 A1 | 12/2004 | Tuschl et al. |
| 2004/0266707 A1 | 12/2004 | Leake et al. |
| 2005/0020521 A1 | 1/2005 | Rana |
| 2005/0171039 A1 | 8/2005 | McSwiggen et al. |
| 2005/0208658 A1 | 9/2005 | Castonguay |
| 2005/0255487 A1 | 11/2005 | Khvorova et al. |
| 2006/0058266 A1 | 3/2006 | Manoharan et al. |
| 2006/0094032 A1 | 5/2006 | Fougerolles et al. |
| 2006/0122136 A1 | 6/2006 | Schubert |
| 2006/0172963 A1 | 8/2006 | Shepard et al. |
| 2006/0172965 A1 | 8/2006 | Shepard et al. |
| 2006/0257851 A1 | 11/2006 | Bentwich |
| 2007/0049543 A1 | 3/2007 | McSwiggen et al. |
| 2007/0050146 A1 | 3/2007 | Bentwich et al. |
| 2007/0093435 A1 | 4/2007 | Andrews et al. |
| 2007/0167384 A1 | 7/2007 | Leake et al. |
| 2009/0326044 A1 | 12/2009 | Shepard et al. |
| 2012/0094374 A1 | 4/2012 | Bentwich et al. |

FOREIGN PATENT DOCUMENTS

| | | |
|---|---|---|
| GB | 2406568 | 4/2005 |
| WO | WO 2003/057840 | 7/2003 |
| WO | WO 2003/059267 | 7/2003 |
| WO | WO 2003/070744 | 8/2003 |
| WO | WO 2003/087367 | 10/2003 |
| WO | WO 2003/092584 | 11/2003 |
| WO | WO 2004/009794 | 1/2004 |
| WO | WO 2004/009796 | 1/2004 |
| WO | WO 2004/029212 | 4/2004 |
| WO | WO 2004/042024 | 5/2004 |
| WO | WO 2005/032493 | 4/2005 |
| WO | WO 2005/044976 | 5/2005 |
| WO | WO 2005/045037 | 5/2005 |
| WO | WO 2005/076998 | 8/2005 |
| WO | WO 2005/079815 | 9/2005 |
| WO | WO 2006/021817 | 3/2006 |
| WO | WO 2006/083945 | 8/2006 |
| WO | WO 2006/084217 | 8/2006 |
| WO | WO 2006/099353 | 9/2006 |
| WO | WO 2008/024983 | 2/2008 |
| WO | WO 2014/037686 | 3/2014 |

OTHER PUBLICATIONS

Achenbach et al., Oligonucleotide-Based Knockdown Technologies: Antisense Versus RNA Interference, ChemBioChem., 4, pp. 928-935, 2003.

"Acuity has New Approach to AMD, Its Drug is Designed to Shut Down VEGF Production" Ophthalmology Management, Apr. 1, 2004, pp. 1-4—cited in AU opposition.

The Agis Investigators, "The Advanced Glaucoma Intervention Study (AGIS): 7. The Relationship Between Control of Intraocular Pressure and Visual Field Deterioration," Am. J. Ophthalmol., 130, pp. 429-440, 2000—Cited in AU Opposition.

Akashi et al., "Suppression of Gene Expression by RNA Interference in Cultured Plant Cells," Antisense Nucleic Acid Drug Dev, 2001, 11(6):359-367.

Amaratunga et al., "Inhibition of Kinesin Synthesis and Rapid Anterograde Axonal Transport in Vivo by An Antisense Oligonucleotide," The Journal of Biological Chemistry, 268(23) pp. 17427-17430, Aug. 15, 1993.

Ambati et al., "Transscleral Delivery of Bioactive Protein to the Choroid and Retina," Investigative Ophthalmology & Visual Science, vol. 41, No. 5, pp. 1186-1191, Apr. 2000.

Ambion, "The Basics: RNase Control," printout from website <<http://web.archive.org/web/20041207234247>>, dated 2004, retrieved on Sep. 17, 2009.

Ambion, Tech Notes 10(4) and siRNA Target Finder (http://www.ambion.com/techlib/misc/siRNA_finder.html, available to the public) retrieved on May 1, 2008, siRNA target hit for SEQ ID No.139 included.

Amended Statement of Grounds and Particulars filed on Jun. 5, 2012 (amending original Grounds filed on Dec. 2, 2010), from opponents in Opposition by Alcon Research, Ltd. against Australian Patent Application No. 2005276245 in the name of Sylentis SAU.

Andrieu-Soler C., et al "Ocular gene therapy: A review of nonviral strategies," Molecular Vision, 12:1334-47, 2006.

Aravin et al., "Role of Double-Stranded RNA in Eukaryotic Gene Silencing," Mol. Biol. (Mosk.), 36(2), pp. 240-51, Mar.-Apr. 2002, Abstract Only.

Banan et al., "The Ins and Outs of RNAi in Mammalian Cells," Current Pharmaceutical Biotechnology, 5, pp. 441-450, 2004.

Banerjee et al., "Control of Developmental Timing by Small Temporal RNAs: a Paradigm for RNA-mediated Regulation of Gene Expression," Bioessays, 2002, 24(2):119-129.

Barar J. et al., "Ocular novel drug delivery impacts of membranes and barriers," *Expert Opin. Drug Deliv.*, 5(5): 567-81, 2008.

Bass, "The Short Answer," Nature, vol. 411, pp. 428-429, 2001.

Bhattacharya et al., "Cochlin Deposits in the Trabecular Meshwork of the Glaucomatous DBA/2J mouse," Exp Eye Res., May 2005 80(5):741-744.

(56) References Cited

OTHER PUBLICATIONS

Bhattacharya et al., "Proteomics Reveal Cochlin Deposits Associated with Glaucomatous Trabecular Meshwork," J. Biol. Chem., Feb. 2005b, 18;280(7):6080-6084, Epub Dec 3. 2004.
Bill, "Movement of Albumin and Dextran," Arch. Opthal., vol. 74, pp. 248-252, Aug. 1965.
Borrás, "Gene Expression in the Trabecular Meshwork and the Influence of Intraocular Pressure," *Progress in Retinal and Eye Research*, 22, 435-463, 2003.
Bosher et al., "RNA Interference: Genetic Wand and Genetic Watchdog." Nat Cell Biol, 2000, 2(2):E31-6.
Braasch et al., "Novel Antisense and Peptide Nucleic Acid Strategies for Controlling Gene Expression," Biochemistry, 2002, 41(14):4503-4510.
Brummelkamp et al., "A System for Stable Expression of Short Interfering RNAs in Mammalian Cells," Science, American Association for the Advancement of Science, 2002, 296(5567):550-553.
Burnett et al., "Current Progress of siRNA/shRNA Therapeutics in Clinical Trials," Biotechnology Journal, vol. 6, No. 9, pp. 1130-1146, Jul. 2011.
Busch et al., "Adenylyl Cyclase in Human and Bovine Trabecular Meshwork," Investigative Ophthalmology & Visual Science, 34(10), pp. 3028-3034, Sep. 1993.
Bunce et al., "Associations between the deletion polymorphism of the angiotensin 1-converting enzyme gene and ocular signs of primary open-angle glaucoma," Graefes Arch Clin Exp Ophthalmol., Apr. 2005 243(4):294-299. Epub Oct. 13, 2004.
Caballero et al., "Inefficient Processing of an Olfactomedin-Deficient Myocilin Mutant: Potential Physiological Relevance to Glaucoma," *Biochemical and Biophysical Research Communications*, 282, 662-670, 2001.
Caplen et al., "Specific inhibition of Gene Expression by Small Double Stranded RNAs in Invertebrate and Vertebrate Systems," Proc. Natl. Acad. Sci. USA, 2001,98: 9742-9747.
Cho et al., "Small Interfering RNA-Induced TLR3 Activation Inhibits Blood and Lymphatic Vessel Growth," PNAS, pp. 1-6, Dec. 5, 2008.
Chudgar et al., "Elevated Intraocular Pressure and Mechanical Stress Increase Connective Tissue Growth Factos Expression in the Trabecular Meshwork," Invest Ophthalmol Vis Sci, 45, E-Abstract 4433, 2004.
Clark et al., "Opthalamic Drug Discovery," Nature Reviews Drug Discover, pp. 448-459, 2003.
Comes N. and Borrás T, "Functional delivery of synthetic naked siRNA to the human trabecular meshwork in perfused organ cultures," *Molec. Vision*, 13:1363-74, 2007.
Costagliola et al., "Effect of Oral Losartan Potassium Administration on Intraocular Pressure in Normotensive and Glaucomatous Human Subjects," Exp Eye Res., Aug. 2000, 71(2):167-171.
Costagliola et al., "Effect of Oral Captopril (SQ 14225) on Intraocular Pressure in Man," Eur. J. Opthalmol, Jan. 1995, 5(1):19-25.
Crooke et al., "Nucleotides in Ocular Secretions: Their Role in Ocular Physiology," Pharmacology & Therapeutics, 119, pp. 55-73, 2008.
Cullinane et al., "Renin-angiotensin System Expression and Secretory Function in Cultured human Ciliary Cody Nonpigmented Epithelium," Br J Ophthalmol. Jun. 2002, 86(6):676-83.
Davson H, "The Aqueous Humour and the Intraocular Pressure," Davson's Physiology of the Eye, 5th edition, Pergamon Press, pp. 3-95, 1990.
Dejneka NS., et al., "Ocular Biodistribution of Bevasiranib Following a Single Intravitreal Injection to Rabbit Eyes," Molecular Vision, 14:997-1005, 2008.
Denkert et al., "Induction of G0/G1 Cell Cycle Arrest in Ovarian Carcinoma Cells by the Ant-Inflammatory Drug NS-398, but not by COX-2-Specific RNA Interference," Oncogene, 2003, 22:8653-8661.

Diffen, DNA vs. RNA—Difference and Comparison, retrieved from <<http://www.diffen.com/difference/Dna_vs_Rna>> on May 21, 2009.
Dinslage et al., "Intraocular Pressure in Rabbits by Telemetry II: Effects of Animal Handling and Drugs," Invest. Ophthalmol Vis Sci., vol. 39(12), pp. 2485-2489, 1998.
Diskin et al., "Detection of Differentially Expressed Glycogenes in Trabecular Meshwork of Eyes with Primary Open-Angle Glaucoma," Investigative Opthalmology & Visual Science, Apr. 2006, 47(4):1491-1499.
Dos Santos ALG., et al "Intraocular Delivery of Oligonucleotides," Current Pharmaceutical Biotechnology, 6:7-15, 2005.
Elabashir et al., "Duplexes of 21-Nucleotide RNAs mediate RNA interference in Cultured Mammalian Cells," Nature, May 24, 2001, 411(6836):494-498.
Elbashir et al., "Functional Anatomy of siRNAs for Mediating Efficient RNAi in *Drosophila melanogaster* Embryo Lysate," EMBO Journal, vol. 20, No. 23, pp. 6877-6888, 2001.
Elbashir et al., "RNA Interference is Mediated by 21- and 22-Nucleotide RNAs," Genes Dev, 2001, 15(2):188-200.
Elena et al., "Autoradiographic Localization of Beta-Adrenergic Receptors in Rabbit Eye," Investigative Ophthalmology & Visual Science, 28, pp. 1436-1441, Aug. 1987.
Epstein et al., "*Effect of Iodoacetamide Perfusion on Outflow Facility and Metabolism of the Trabecular Meshwork*," Invest. Ophthalmol. Vis. Sci., 625-631, May 1981.
Fattal et al., "Ocular Delivery of Nucleic Acids: Antisense Oligonucleotides, Aptamers and siRNA," Advanced Drug Delivery Reviews, 2006, 58:1203-1223.
Fire et al., "Potent and Specific Genetic Interference by Double Stranded RNA in a Caenorhabditis Elegans," Nature, 1998, 391(6669):806-11.
Freier et al., "The Ups and Downs of Nucleic Acid Duplex Stability: Structure-Stability Studies on Chemically-Modified DNA:RNA Duplexes," Nucleic Acids Research, 25(22), pp. 4429-4443, 1997.
Fuchshofer et al., "The Effect of TGF-β2 on Human Trabecular Meshwork Extracellular Proteolytic System," Experimental Eye Research, 77, pp. 757-765, 2003.
Ganesh Prasanna, Ph.D., Resume, 12 pages, May 18, 2012.
Statutory Declaration of Ganesh Prasanna, 19 pages, Jun. 1, 2012.
Ge et al., "RNA Interference of Influenza Virus Production by Directly Targeting mRNA for Degradation and Indirectly Inhibiting all Viral RNA Transcription," Proc Natl Acad Sci USA., 2003, 100(5):2718-2723.
Ghate D. and Edelhauser H.F., "Barriers to glaucoma drug delivery," *J. Glaucoma*, 17(2), 147-56, 2008.
Gil et al., "Induction of Apoptosis by the dsRNA-dependent Protein Kinase (PKR): Mechanism of Action," Apoptosis, 2000, 5(2):107-114.
Gonzalez et al., "Genes Upregulated in the Human Trabecular Meshwork in Response to Elevated Intraocular Pressure," Investigative Opthalmology & Visual Science, Feb. 2000, 41(2):352-361.
Grosshans et al., "Micro-RNAs: Small is Plentiful," J Cell Bioi, 2002, 156(1):17-21.
Hammond et al., "Post-Transcriptional Gene Silencing by Double-Standed RNA," Nature, 2001, 2:110-119.
Hara et al., "Bunazosin, a Selective Alpha1-Adrenoceptor Antagonist, as an Anti-glaucoma Drug: Effects on Ocular Circulation and Retinal Neuronal Damage," Cardiovasc Drug Rev. 2005 Spring;23(1):43-56.
Hart WM, "Intraocular Pressure," Chapter 8, Adler's Physiology of the Eye: Clinical Application, Mosby-Year Book Inc., 9th edition, pp. 248-267, 1992.
Herkel et al., "Update on Topical Carbonic Anhydrase Inhibitors," Current Opinion in Ophthamology, Apr. 2001, 12(2):88-93.
Hogeboom et al., "Angiotensin Converting Enzyme Inhibiting Therapy is Associated with Lower Vitreous Vascular Endothelial Growth Factor Concentrations in Patients with Proliferative Diabetic Retinopathy," Diabetologia, vol. 45, pp. 203-209, 2002.
Horinouchi et al., "Pharmacological Evaluation of Ocular β-Adrenoceptors in Rabbit by Tissue Segment Binding Method," Life Sciences, 84, pp. 181-187, 2009.

(56) References Cited

OTHER PUBLICATIONS

Jens Kurreck, "Antisense Technologies," Eur. J. Biochem., 270, pp. 1628-1644, 2003.
Jens Kurreck, "Antisense and RNA Interference Approaches to Target Validation in Pain Research," Current Opinion in Drug Discovery & Development, 7(2), pp. 179-187, 2004.
Jiménez et al., "Efficacy of Topically Administered siRNAs in Glaucoma Treatment: In vivo Results in Hypertensive Model," Investigative Ophthalmology & Visual Science, 50, E-Abstract 4054, 2009.
Jiménez et al., "$Na^+/K^+$ ATPase: A New Target for Treating Ocular Hypertension by RNAi," Investigative Ophthalmology & Visual Science, 48, E-Abstract 4809 2007.
Jiménez et al., "SYL04003: A New Therapeutic Candidate for Treating Ocular Hypertension using RNAi Technology," Investigative Ophthalmology & Visual Science, 49, E-Abstract 1643, 2008.
Jiménez et al., "SYL040012 A New siRNA-Based Treatment for Glaucoma: Pharmacokinetics and Mechanism of Action," Investigative Ophthalmology & Visual Science, 51, E-Abstract 176, 2010.
Kaplan et al., "Aqueous Humor Flow in Unilateral Carotid Stenosis," Journal of Glaucoma, 5, pp. 237-240, 1996.
Khaw et al., "Glaucoma-1: Diagnosis," BMJ, 2004a, 328:97-99.
Khaw et al., "Glaucoma-2: Treatment," BMJ, 2004, 328:156-158.
Kim et al., "Inhibition of Ocular Angiogenesis by Sirna Targeting Vascular Endothelial Growth Factor Pathway Genes Therapeutics Strategy for Herpetic Stromal Keratititis," American Journal of Pathology, Dec. 2004, 165(6):2177-285.
Krohn et al., "Transcorneal Flux of Topical Pilocarpine to the Human Aqueous," Am. J. Ophthalmol., 87(1), pp. 50-56, Jan. 1979, Abstract retrieved from <<http://www.ncbi.nlm.nih.gov/pubmed/434053>> on Nov. 9, 2009.
Krutzfeldt et al., "Silencing of microRNAs in vivo with 'Antagomirs'," Nature, 2005, 438(7068):685-689.
Kwon et al., "Primary Open-Angle Glaucoma," The New England Journal of Medicine, 360(11), pp. 1113-1124, Mar. 12, 2009.
Liao et al., "Expression of Cell Surface Transmembrane Carbonic Anhydrase Genes CA9 and CA12 in the Human Eye: Overexpression of CA12 (CAXII) in Glaucoma," J. Med. Genet, 40, 257-262, 2003.
Lograno et al., "Receptor-Responses in Fresh Human Ciliary Muscle," Br. J. Pharmac., 87, pp. 379-385, 1986.
Madsen, "Ocular Finding in 123 Patients with Proliferative Diabetic Retinopathy," Documenta Ophthalmologica, Advances in ophthalmology, May 14, 1971, 29(2):345-349.
Mahato et al., "Modulation of Gene Expression by Antisense and Antigene Oligodeoxynucleotides and Small Interfering RNA," Expert Opinion on Drug Delivery, Jan. 2005, 2(1):3-28.
Martin-Gil et al., "Silencing of P2Y2 Receptors Reduces Intraocular Pressure in New Zealand Rabbits," British Journal of Pharmacology, vol. 165, pp. 1163-1172, Feb. 2012.
Martinez et al., In Vitro and in Vivo Efficacy of SYL040012, a Novel siRNA Compound for Treatment of Glaucoma, Molecular Therapy, vol. 22, No. 1, pp. 81-91, 2014.
Meade et al., "Enhancing the Cellular Uptake of siRNA Duplexes Following Noncovalent Packaging with Protein Transduction Domain Peptides," Advanced Drug Delivery Reviews, 60, pp. 530-536, 2008.
Mediero et al., "New Treatments for Ocular Hypertension," Autonomic Neuroscience: Basic and Clinical, vol. 147, No. 1-2, pp. 14-19, May 2009.
Miller et al., "Allele-specific Silencing of Dominant Disease Genes," Proceedings of the National Academy of Sciences of USA, Jun. 10, 2003, 100(12):7195-7200.
Mirshahi et al., "The Mineralocorticoid Hormone Receptor and Action in the Eye," Biochem Biophys Res Commun, vol. 219, pp. 150-156, 1996.
Moreno-Montanes et al., "Phase I Clinical Trial of SYL040012, a Small Interfering RNA Targeting Beta-Adrenergic Receptor 2, for Lowering Intraocular Pressure," Molecular Therapy, vol. 22, pp. 226-232, 2014.
Muratovska et al., "Conjugate for Efficient Delivery of Short Interfering RNA (siRNA) into Mammalian Cells," FEBS Letters, 558, pp. 63-68, 2004.
Nakamura et al., "RNA Interference Targeting Transforming Growth Factor-$\beta$ type II Receptor Suppresses Ocular Inflammation and Fibrosis," Molecular Vision, 10, pp. 703-711, 2004.
Nie Y., et al., "The potential therapeutic of siRNA eye drops in ocular diseases," *Bioscience Hypotheses*, 2, 223-25, 2009.
Okabe et al., "Effect of Benzalkonium Chloride on Transscleral Drug Delivery," Investigative Ophthalmology & Visual Science, vol. 46, No. 2, pp. 703-708 , Feb. 2005.
Olsen et al., "Human Scleral Permeability: Effects of Age, Cryotherapy, Transscleral Diode Laser, and Surgical Thinning," Investigative Ophthalmology & Visual Science, vol. 36, No. 9. pp. 1893-1903, Aug. 1995.
Osborne et al., "Some Current Ideas on the Pathogenesis and the Role of Neuroprotection in Glaucomatous Optic Neuropathy," Eur J Ophthalmol., Apr. 2003, 13Suppl. 3:S19-26.
Paddison et al., "Short hairpin RNAs (shRNAs) Induce Sequence-Specific Silencing in Mammalian Cells," Genes Dev, 2002, 16(8):948-958.
Papers filed on Mar. 2, 2012, from opponents in Opposition by Alcon Research, Ltd. against Australian Patent Application No. 2005276245 in the name of Sylentis SAU.
Peral et al., "Effect of Several siRNA in the Treatment of Ocular Hypertension and Glaucoma," Invest. Ophthalmol. Vis. Sci., 48, E-Abstract 4808, 2007.
Pintor et al., "Adenosine Tetraphosphate, $Ap_4$, a Physiological Regulator of Intraocular Pressure in Normotensive Rabbit Eyes," The Journal of Pharmacology and Experimental Therapeutics, vol. 308, No. 2, pp. 468-473, 2004.
Pintor, "Silencing Beta2-Adrenergic Receptors Reduces Intraocular Pressure: A New Approach for Glaucoma Therapy," Anales De La Real Academia Nacional De Farmacia, vol. 78, No. 2, pp. 230-240, Jun. 2012.
Pintor et al., "SiRNA in the Treatment of Ocular Hypertension Targeting Alpha and Beta Adrenoceptors," Invest. Ophthalmol. Vis. Sci., 47, E-Abstract 403, 2006.
Rao et al., "Modulation of Aqueous Humor Outflow Facility by the Rho Kinase-Specific Inhibitor Y-27632," Investigative Opthalmology & Visual Science, Apr. 2001, 42(5): 1029-1037.
Reich et al., "Small Interfering RNA (siRNA) Targeting VEGF effectively Inhibits Ocular Neovascularization in a Mouse Model," Molecular Vision, 2003, 9:210-216.
Ruz et al., "Phase I Study With a New siRNA: SYL040012. Tolerance and Effect on Intraocular Pressure," Investigative Ophthalmology Visual Science, 52, E-Abstract 223, 2011.
Sakaguchi et al., "Chymase and Angiotensin Converting Enzyme Activities in a Hamster Model of Glaucoma Filtering Surgery," Curr Eye Res., May 2002, 24(5):325-331.
Scherer et al., "Approaches for the Sequence-Specific Knockdown of mRNA," Nat. Biotechnology, 2003, 21(12):1457-1465.
Shah et al., "Oculohypotensive Effect of Angiotensin-Converting Enzyme Inhibitors in Acute and Chronic Models of Glaucoma," J Cardiovasc Pharmacol. Aug. 2000, 36(2):169-175.
Stamer et al., "Isolation and Culture of Human Trabecular Meshwork Cells by Extracellular Matrix Digestion," Current Eye Research, pp. 611-617, Jan. 10, 1995.
Studies conducted in the Biochemistry Department of the School of Optics at the Universidad Complutense de Madrid, as filed in the Information Disclosure Statement of Oct. 30, 2008 (in U.S. Appl. No. 11/574,169).
Supuran et al., "Carbonic Anhydrase Inhibitors," Medicinal Research Reviews, 23(2):146-189, 2003.
Tan et al., "Recent Developments in Understanding the Pathophysiology of Elevated Intraocular Pressure," Current Opinion in Opthalmology, vol. 17, pp. 168-174, 2006.
Tolentino et al., "Intravitreal Injection of Vascular Endothelial Growth Factor Small Interfering RNA Inhibits Growth and Leakage in a Nonhuman Primate, Laser-Induced Model of Chorodial Neovascularization," Retina, The Journal of Retinal and Vitreous Diseases, vol. 24, No. 1, 2004, pp. 132-138.

(56) References Cited

OTHER PUBLICATIONS

Tuschl et al., "Targeted mRNA degradation by double-stranded RNA in vitro," Genes Dev., 1999, 13(24):3191-3197.
Uprichard et al., The Therapeutic Potential of RNA Interference, FEBS Letters, Oct. 31, 2005 579(26):5996-6007.
Valls et al., "Validation of a Device for Transcorneal Drug Permeation Measure," Journal of Pharmaceutical and Biomedical Analysis, 48, pp. 657-663, 2008.
Vittal et al., "Changes in Gene Expression by Trabecular Meshword Cells in Response to Mechanical Stretching," Investigative Opthalmology & Visual Science, Aug. 2005, 46(8):2857-2868.
Wang et al., Effect of C5-088, an Angiotensin AT1 Receptor Antagonist, on Intraocular Pressure in Glaucomatous Monkey Eyes, Exp Eye Res., May 2005 80(5):629-632. Epub Jan 4, 2005.
Wax et al., "Vacuolar $H^+$-ATPase in Ocular Ciliary Epithelium," Proc. Natl. Acad. Sci., vol. 94, pp. 6752-6757, Jun. 1997.
Wetering et al., "Specific Inhibition of Gene Expression Using a Stably Integrated, Inducible Small-Interfering-RNA Vector," EMBO Reports, Jun. 2003, 4(6):609-615.
Wianny et al., "Specific Interference with Gene Function by Double-Stranded RNA in Early Mouse Development," Nat Cell Biol, 2000, 2(2):70-75.
Williams BR, "Role of the Double-Stranded RNA-activated Protein kinase (PKR) in Cell Regulation," Biochem Soc Trans, 1997, 25(2):509-513.
Wirtz et al., "The Genetic Loci of Open-Angle Glaucoma," Ophthalmol. Clin. North Am. 2003 16:505-514.
Wiznerowicz et al., "Conditional Suppression of Cellular Genes: Lentivirus Vector-Mediated Drug-Inducible RNA Interference," Journal of Virology, Aug. 2003, 77(16):8957-8961.
Woodward et al., "The Inflow and Outflow of Anti-Glaucoma Drugs," Trends in Pharmacological Sciences, May 2004, 25(5):238-241.
Xie et al., "Harnessing in vivo siRNA Delivery for Drug Discovery and Therapeutic Development," Drug Discovery Today, Jan. 2006, 11(1-2):67-73.
Yang-Feng et al., "Chromosomal Organization of Adrenergic Receptor Genes," PNAS, 1990, 87:1516-1520.
Yang et al., "Early Growth Response Gene 1 Modulates Androgen Receptor Signaling in Prostate Carcinoma Cells," The Journal of Biological Chemistry, 278(41), pp. 39906-39911, 2003.
Yan et al., "Requirement of NeuroD for Photoreceptor Formation in the Chick Retina," Invest Ophthalmol Vis. Sci., 45(1), pp. 48-58, Jan. 2004.
Zhang et al., "Ophthalmic Drug Discovery: Novel Targets and Mechanisms for Retinal Diseases and Glaucoma," Nature Reviews Drug Discovery, vol. 11, No. 7, pp. 541-559, Jun. 2012.
Jimenez et al., Office Action dated Jul. 14, 2008 in corresponding U.S. Appl. No. 11/360,305, 18 pages.
Jimenez et al., Office Action dated Jan. 29, 2009 in corresponding U.S. Appl. No. 11/360,305, 11 pages.
Jimenez et al., Office Action dated Nov. 12, 2008 in corresponding U.S. Appl. No. 11/574,169, 12 pages.
Jimenez et al., Final Office Action dated May 8, 2009 in corresponding U.S. Appl. No. 11/574,169, 11 pages.
Jimenez et al., Office Action dated Nov. 3, 2009 in corresponding U.S. Appl. No. 12/170,078, 10 pages.
Jimenez et al., Office Action dated Oct. 15, 2009 in corresponding U.S. Appl. No. 12/170,104, 12 pages.
Jimenez et al., Office Action dated Oct. 15, 2009 in corresponding U.S. Appl. No. 12/170,157, 12 pages.
Jimenez et al., Office Action dated Oct. 30, 2009 in corresponding U.S. Appl. No. 12/170,116, 12 pages.
Jimenez et al., Office Action dated Oct. 30, 2009 in corresponding U.S. Appl. No. 12/170,132, 10 pages.
Jimenez et al., Office Action dated Oct. 19, 2009 in corresponding U.S. Appl. No. 12/170,148, 11 pages.
Jimenez et al., Office Action dated Dec. 4, 2009 in corresponding U.S. Appl. No. 11/574,169, 16 pages.
Jimenez et al., Office Action dated Mar. 19, 2010 in corresponding U.S. Appl. No. 12/170,078, 12 pages.
Jimenez et al., Office Action dated Mar. 22, 2010 in corresponding U.S. Appl. No. 12/170,104, 14 pages.
Jimenez et al., Office Action dated Mar. 19, 2010 in corresponding U.S. Appl. No. 12/170,116, 13 pages.
Jimenez et al., Office Action dated Mar. 22, 2010 in corresponding U.S. Appl. No. 12/170,132, 12 pages.
Jimenez et al., Office Action dated Mar. 22, 2010 in corresponding U.S. Appl. No. 12/170,148, 13 pages.
Jimenez et al., Office Action dated Mar. 22, 2010 in corresponding U.S. Appl. No. 12/170,157, 14 pages.
Jimenez et al., Office Action dated Mar. 25, 2010 in corresponding U.S. Appl. No. 12/563,530, 21 pages.
Jimenez et al., Final Office Action dated Jul. 22, 2010 in corresponding U.S. Appl. No. 11/574,169, 22 pages.
Jimenez et al., Office Action dated Sep. 7, 2010 in corresponding U.S. Appl. No. 11/574,169, 25 pages.
Jimenez et al., Office Action dated Sep. 23, 2010 in corresponding U.S. Appl. No. 12/170,078, 27 pages.
Jimenez et al., Office Action dated Sep. 23, 2010 in corresponding U.S. Appl. No. 12/170,104, 31 pages.
Jimenez et al., Office Action dated Sep. 23, 2010 in corresponding U.S. Appl. No. 12/170,116, 30 pages.
Jimenez et al., Office Action dated Sep. 23, 2010 in corresponding U.S. Appl. No. 12/170,132, 28 pages.
Jimenez et al., Response to Nonfinal Office Action dated Jul. 14, 2008, filed electronically Nov. 14, 2008 for U.S. Appl. No. 11/360,305, 40 pages.
Jimenez et al., Office Action dated Sep. 23, 2010 in corresponding U.S. Appl. No. 12/170,148, 28 pages.
Jimenez et al., Office Action dated Sep. 23, 2010 in corresponding U.S. Appl. No. 12/170,157, 31 pages.
Jimenez et al., Office Action dated Aug. 10, 2011 in corresponding U.S. Appl. No. 12/091,498, 11 pages.
Jimenez et al., Office Action dated Mar. 19, 2012 in corresponding U.S. Appl. No. 12/170,104, 16 pages.
Jimenez et al., Office Action dated Mar. 19, 2012 in corresponding U.S. Appl. No. 12/170,116, 16 pages.
Jimenez et al., Office Action dated Mar. 19, 2012 in corresponding U.S. Appl. No. 12/170,132, 16 pages.
Jimenez et al., Office Action dated Mar. 19, 2012 in corresponding U.S. Appl. No. 12/170,148, 16 pages.
Jimenez et al., Office Action dated Mar. 19, 2012 in corresponding U.S. Appl. No. 12/170,157, 16 pages.
Jimenez Anton et al., Office Action dated Aug. 3, 2016 in corresponding U.S. Appl. No. 14/425,466, 15 pages.
Jimenez Anton et al., Office Action dated Nov. 12, 2015 in corresponding U.S. Appl. No. 14/425,466, 13 pages.
EU Clinical Trials Register, EudraCT No. 2011-001849-33, Estonia, EEA CTA, Mar. 8, 2012, 7 pages.
EU Clinical Trials Register, EudraCT No. 2011-001849-33, Spain, EEA CTA, Mar. 20, 2012, 8 pages.
EU Clinical Trials Register, EudraCT No. 2011-001849-33, Germany, EEA CTA, May 21, 2012, 7 pages.
U.S. Appl. No. 11/574,169, filed Jul. 16, 2007, Ana Jimenez et al., U.S. Pat. No. 8,030,284, Oct. 4, 2011.
U.S. Appl. No. 11/360,305, filed Feb. 22, 2006, Ana Jimenez et al., U.S. Pat. No. 7,592,325, Sep. 22, 2009.
U.S. Appl. No. 12/170,078, filed Jul. 9, 2008, Ana Jimenez et al., U.S. Pat. No. 8,198,250, Jun. 12, 2012.
U.S. Appl. No. 12/170,104, filed Jul. 9, 2008, Ana Jimenez et al., U.S. Pat. No. 8,247,386, Aug. 21, 2012.
U.S. Appl. No. 12/170,116, filed Jul. 9, 2008, Ana Jimenez et al., U.S. Pat. No. 8,247,387, Aug. 21, 2012.
U.S. Appl. No. 12/170,132, filed Jul. 9, 2008, Ana Jimenez et al., U.S. Pat. No. 8,258,110, Sep. 4, 2012.
U.S. Appl. No. 12/170,148, filed Jul. 9, 2008, Ana Jimenez et al., U.S. Pat. No. 8,252,758, Aug. 28, 2012.
U.S. Appl. No. 12/170,157, filed Jul. 9, 2008, Ana Jimenez et al., U.S. Pat. No. 8,252,759, Aug. 28, 2012.
U.S. Appl. No. 12/563,530, filed Sep. 21, 2009, Ana Jimenez et al., U.S. Pat. No. 7,902,169, Mar. 8, 2011.

(56) References Cited

OTHER PUBLICATIONS

U.S. Appl. No. 12/874,928, filed Sep. 2, 2010, Ana Jimenez et al., U.S. Pat. No. 8,389,490, Mar. 5, 2013.
U.S. Appl. No. 13/744,881, filed Jan. 18, 2013, Ana Jimenez et al., U.S. Pat. No. 8,951,982, Feb. 10, 2015.
U.S. Appl. No. 14/425,466, filed Mar. 3, 2015, Ana Jimenez Anton et al.
U.S. Appl. No. 14/425,459, filed Mar. 3, 2015, Ana Jimenez Anton et al.
Bian et al., "High-Dose siRNAs Upregulate Mouse Eri-1 at both Transcription and Posttranscription Levels," PLoS One, 6(10), pp. 1-15, 2011.
Coelho et al., "Safety and Efficacy of RNAi Therapy for Transthyretin Amyloidosis," N. Engl. J. Med. 369(9), pp. 819-829, 2013.
Gonzalez et al., "Phase 2 of Bamosiran (SYL040012), a Novel RNAi Based Compound for the Treatment of Increased Intraocular Pressure Associated to Glaucoma," Investigative Ophthalmology & Visual Science, vol. 55, 564, Apr. 2014, including ARVO Annual Meeting Abstract poster.
González et al., "Bamosiran ophthalmic solution for the treatment of glaucoma: Results of the Phase IIB SYLTAG study," 2016 Annual Meeting in Seattle, Wash. May 1-5, 2016 (poster presented on May 3, 2016).
Moreno-Montanes et al., "Phase I Clinical Trial of SYL040012,a Small Interfering RNA Targeting β-Adrenergic Receptor 2, for Lowering Intraocular Pressure," Molecular Therapy, vol. 22, No. 1, pp. 226-232, 2014.
Pecot et al., "RNA interference in the clinic: challenges and future directions," Nature Reviews, 11, pp. 59-67, 2011.
What are the Symptoms of Glaucoma? Writtenby Kierstan Boyd (downloaded from https://www.aao.org/eye-health/diseases/glaucoma-symptoms, on Oct. 31, 2017, 4 pages.

SEQ ID NO: 1
Human ADRB2 mRNA target sequence: CAUUGUGCAUGUGAUCCAG
SEQ ID NO: 2

| SYL040012: Sense | 5' - <u>CAUUGUGCAUGUGAUCCAG</u> dT dT - 3' |
|---|---|
| Antisense | 3'- dT dT <u>GUAACACGUACACUAGGUC</u> - 5' |

SEQ ID NO: 3

| Sense | 5' - <u>CAUUGUGCAUGUGAUCCAG</u>- 3' |
|---|---|
| Antisense | 3'- <u>GUAACACGUACACUAGGUC</u> - 5' |

SEQ ID NO: 4

| Sense | 5' - <u>CAUUGUGCAUGUGAUCCAG</u> - 3' |
|---|---|
| Antisense | 3'- dT dT <u>GUAACACGUACACUAGGUC</u> - 5' |

SEQ ID NO: 5

| Sense | 5' - <u>CAUUGUGCAUGUGAUCCAG</u> dT dT - 3' |
|---|---|
| Antisense | 3'- <u>GUAACACGUACACUAGGUC</u> - 5' |

SEQ ID NO: 6

| Sense | 5' - <u>CAUUGUGCAUGUGAUCCAG</u> dU dU - 3' |
|---|---|
| Antisense | 3'- dU dU <u>GUAACACGUACACUAGGUC</u> - 5' |

Underline represents hybridization region

Figure 5

SEQUENCE LISTING

```
<160> NUMBER OF SEQ ID NOS: 6

<210> SEQ ID NO 1
<211> LENGTH: 19
<212> TYPE: RNA
<213> ORGANISM: Homo sapiens

<400> SEQUENCE: 1
cauugugcau gugauccag                                                    19

<210> SEQ ID NO 2
<211> LENGTH: 21
<212> TYPE: DNA
<213> ORGANISM: Artificial
<220> FEATURE:
<223> OTHER INFORMATION: SYL040012 - short Interfering nucleic acid
      (siNA)
<220> FEATURE:
<221> NAME/KEY: misc_feature
<223> OTHER INFORMATION: SEQ ID NO: 2 represents the sense strand of a
      double stranded molecule

<400> SEQUENCE: 2
cauugugcau gugauccagt t                                                 21

<210> SEQ ID NO 3
<211> LENGTH: 19
<212> TYPE: RNA
<213> ORGANISM: Artificial
<220> FEATURE:
<223> OTHER INFORMATION: short interfering nucleic acid
<220> FEATURE:
<221> NAME/KEY: misc_feature
<223> OTHER INFORMATION: SEQ ID NO: 3 represents the sense strand of a
      double stranded molecule

<400> SEQUENCE: 3
cauugugcau gugauccag                                                    19

<210> SEQ ID NO 4
<211> LENGTH: 19
<212> TYPE: RNA
<213> ORGANISM: Artificial
<220> FEATURE:
<223> OTHER INFORMATION: short interfering nucleic acid
<220> FEATURE:
<221> NAME/KEY: misc_feature
<223> OTHER INFORMATION: SEQ ID NO: 4 represents the sense strand of a
      double stranded molecule

<400> SEQUENCE: 4
cauugugcau gugauccag                                                    19

<210> SEQ ID NO 5
<211> LENGTH: 21
<212> TYPE: DNA
<213> ORGANISM: Artificial
<220> FEATURE:
<223> OTHER INFORMATION: short interfering nucleic acid
```

```
<220> FEATURE:
<221> NAME/KEY: misc_feature
<223> OTHER INFORMATION: SEQ ID NO: 5 represents the sense strand of a
      double stranded molecule

<400> SEQUENCE: 5
cauugugcau gugauccagtt                                                    21

<210> SEQ ID NO 6
<211> LENGTH: 21
<212> TYPE: RNA
<213> ORGANISM: Artificial
<220> FEATURE:
<223> OTHER INFORMATION: short interfering nucleic acid
<220> FEATURE:
<221> NAME/KEY: misc_feature
<223> OTHER INFORMATION: SEQ ID NO: 6 represents the sense strand of a
      double stranded molecule

<400> SEQUENCE: 6
cauugugcau gugauccaguu                                                    21
```

SIRNAS AND THEIR USE IN METHODS AND COMPOSITIONS FOR THE TREATMENT AND/OR PREVENTION OF EYE CONDITIONS

BACKGROUND OF THE INVENTION

Glaucoma is defined as the process of ocular tissue destruction caused by a sustained elevation of intra ocular pressure (IOP) above its normal physiological limits[1]. In open angle glaucoma (OAG), elevated IOP causes a progressive optic neuropathy due to loss of retinal ganglion cells that ultimately leads to blindness[2]. In angle-closure glaucoma the sudden high rise in IOP often renders the eye blind. Glaucoma is the second leading cause of blindness worldwide[3] and the prevalence is increasing worldwide[4]. Blindness in glaucoma is caused by a degenerative process of the retina and optic nerve, but is functionally associated with impairments in the balance between aqueous humor (AH) secretion and outflow. AH is secreted by cells of the ciliary body (CB) and outflow can occur through one of two pathways: the trabecular meshwork pathway and the uveoscleral pathway[5].

Current treatment for glaucoma is not able to restore vision-loss caused by glaucoma, but is focused on IOP reduction[6]. Controlling IOP has been shown to protect against damage to the optic nerve in glaucoma[5,7]. There are five drug classes currently used to achieve IOP reduction: α-adrenergic agonists, β-adrenergic antagonists, cholinergic agonists, prostaglandins and carbon anhydrase inhibitors. If no efficacy in reducing IOP is achieved with any of these drugs, laser therapy can be applied to the trabecular meshwork in order to increase AH outflow. The last therapeutic resource is a surgical procedure to create a new route for AH outflow[8].

Current treatments for increased IOP associated with glaucoma have relatively few ocular side effects but may have systemic side effects if the compound reaches the bloodstream[9,10,11]. Treatments that are systemically better tolerated, such as prostaglandins, have many local tolerance issues[12]. This fact together with the required frequency of instillations in order to maintain adequate levels of IOP makes treatment compliance a challenge for patients[13]. Failure to comply with therapy cannot only allow for disease progression but can also have a reboot effect causing sudden increases in IOP that can be very damaging to the optic nerve.

Prostaglandins and beta-blockers are the preferred IOP-lowering agents.[12,14] Prostaglandins lower IOP extremely well and are safe systemically but have several associated ocular side effects,[15] i.e., darkening of the iris color, lash growth, periocular pigmentation, and hyperemia. Less frequent ocular side effects of this drug class are intraocular inflammation, cystoid macular edema, and reactivation of ocular corneal herpes viral infections[16]. Prostaglandin analogs are contraindicated during pregnancy because of the potential risk of premature labor.

Topical application of beta blockers reduces IOP by decreasing AH production and not by increasing its outflow. Topically administered beta-blockers are absorbed via the conjunctival epithelium, lacrimal channel, nasal mucosa and gastrointestinal tract into the systemic circulation inducing systemic adverse reactions[17-19]. In the eye, adrenergic receptors have been located at blood vessels that irrigate the ciliary body and trabecular meshwork, where their main effect is vasoconstriction, although their involvement in aqueous humor secretion has also been described. Previous studies in rabbits' eyes showed high density of β-adrenergic receptors in conjunctival, corneal and ciliary process epithelium. β-adrenergic receptors were also present in corneal endothelium, lens epithelium, choroid and extraocular muscle. Most of the β-adrenergic receptors detected in eye belong to the β2-type[20-23].

RNA interference (RNAi) is a technology based on the principle that small, specifically designed, chemically synthesized double-stranded RNA fragments can mediate specific messenger RNA (mRNA) degradation in the cytoplasm and hence selectively inhibit the synthesis of specific proteins. This technology has emerged as a very powerful tool to develop new compounds aimed at blocking and/or reducing anomalous activities in defined proteins[24,25]. Compounds based on RNA interference can be rationally designed to block expression of any target gene, including genes for which traditional small molecule inhibitors cannot be found[26]. Examples of successful use of RNAi in therapeutics include inhibition of HIV-1 replication in human cells[27] and knock-down of tau and apolipoprotein precursor protein in animal models of Alzheimer's disease[28]. Even though RNAi was discovered just over a decade ago, a few of these compounds are already in advanced phases of clinical trials, i.e., ALN-TTR02 (Alnylam Pharmaceuticals, phase III) for treating TTR Amyloidosis, PF-04523655 (Quarck Pharmaceuticals and Pfizer, phase IIb) for treating diabetic macular edema, and ARC-520 (Arrowhead Research, phase IIa) for treating hepatitis B virus infection. RNA interference is a very attractive approach to chronic conditions, since upon cessation of treatment the silenced protein has to be re-synthesized in order to recover its biological activity. Hence the effects of compounds based on RNA interference are in general more prolonged than those of conventional treatments[24, 29].

The eye is a relatively isolated tissue compartment; this particularity provides several advantages to the use of siRNA based therapies. Local delivery of compounds to the eye limits systemic exposure and reduces the amount of compound needed. This allows for local silencing of a gene and reducing the likelihood of wide spread silencing outside the eye. In addition, the immune system has a limited access to the eye; therefore immune responses to the compound are less likely to occur[30].

Continuing the work described in WO2006/021817, we have developed an siRNA: SYL040012, with the nucleotide sequence of SEQ ID NO: 2, a chemically synthesized, unmodified, 19 bp double-stranded oligonucleotide with dinucleotide overhangs at the 3' ends of each strand of deoxythymidine, able to selectively inhibit synthesis of β2-adrenergic receptor, indicated for the treatment of elevated IOP in patients with ocular hypertension, open angle glaucoma, and other related diseases.

The compound has proven efficacy inhibiting expression of its target in cell cultures and in lowering IOP in normotensive rabbits and in a model of increased IOP in rabbits.

BRIEF DESCRIPTION OF THE FIGURES

FIG. 5: siNA molecules of the invention. This figure shows oligonucleotides sequences for siNA molecules encompassed in the present invention.

SUMMARY OF THE INVENTION

Figure 1:
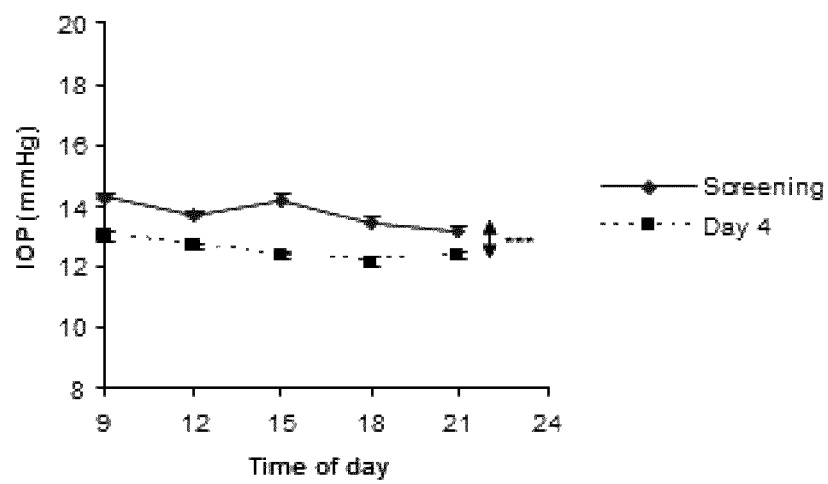
FIG. 1: IOP curves in response to doses A and B of SYL040012. A. IOP evolution in 12 healthy subjects in response to repeated administration of dose A of SYL040012; B. TOP evolution in the subgroup of subjects that showed a decrease in IOP greater than 20% in response to dose A of SYL040012 (n=5). C: IOP evolution in 12 healthy subjects in response to repeated administrations of dose B of SYL040012. Data represent mean±standard error of the mean (s.e.m) of 12 subjects in A and C and 5 subjects in B. Statistical significance was calculated by Repeated Measures two-way ANOVA and Bonferroni's corrections were made for the subsequent pairwise comparisons and was as follows: *p<0.001; p<0.01 and *p<0.05.
Figure 1:
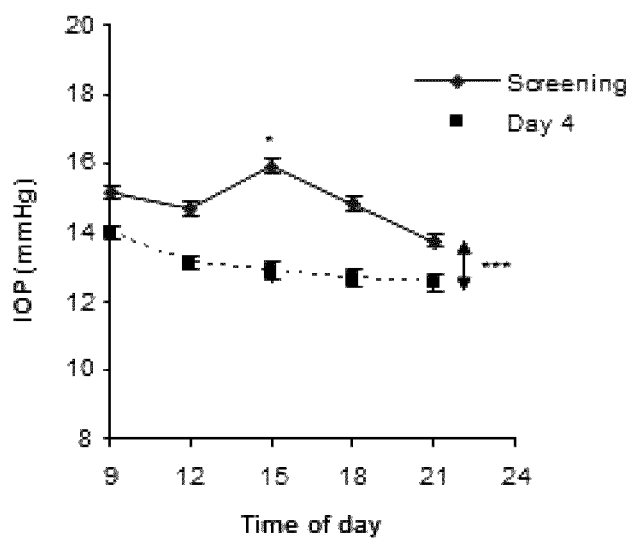

The present invention relates to methods, compositions and dosages that decrease IOP of the eye, comprising SYL040012, a 19 nucleotide double-stranded RNA molecule with dinucleotide deoxythymidine overhangs at 3'. The compositions of the present invention comprise SYL040012 in a saline solution such as PBS and pharmaceutically acceptable excipients, thus allowing their instillation on the eye, i.e. as eyedrops. The dosages of the invention comprise a daily instillation of an eyedrop of between about 25 μl and about 40 μl, comprising between about 0.08 mg and about 0.9 mg of SYL040012 per eye per day.

The present invention relates to methods, compositions and dosages that decrease IOP of the eye. The compositions of the invention comprise short interfering nucleic acid molecules (siNA) that decrease expression of adrenergic receptor beta 2 (ADRB2) gene, which, as indicated previously, decreases production of aqueous humor within the anterior chamber of the eye. The compositions of the invention can be used in the preparation of a medicament for the treatment of an eye condition displaying increased IOP such as glaucoma, infection, inflammation, uveitis, and diabetic retinopathy. The methods of the invention comprise the administration to a patient in need thereof of an effective amount of one or more siNAs of the invention in an effective dosing regimen.

The compositions of the invention comprise short interfering nucleic acid molecules (siNA) that decrease or inhibit expression of adrenergic receptor beta 2 (ADRB2), a gene associated with production of intraocular fluid, i.e. aqueous humor. The present invention encompasses compositions and methods of use of short interfering nucleic acid (siNA) including, but not limited to, short interfering RNA (siRNA), double-stranded RNA (dsRNA), and short hairpin RNA (shRNA) molecules capable of mediating RNA interference (RNAi) against the target gene, ADRB2. In preferred embodiments, the siNA used in the methods of the invention are dsRNA. siNAs of the invention can be unmodified or chemically modified.

The methods of the invention comprise the administration to a patient in need thereof of an effective amount of at least an siNA of the invention. In preferred embodiments the methods of the invention provide a sustained decrease in IOP when compared with the duration of IOP decrease which results from administration of commercially available drugs such as Xalatan, Trusopt and Timoftol. In a preferred embodiment, the siNA is SYL040012.

Methods of the invention also encompass administration of one or more siNAs of the invention in combination with one or more other therapeutics that decrease IOP including, but not limited to, commercially available drugs. In specific embodiments, the methods encompass administration of only one siNA species, which is preferably SYL040012.

Methods or uses of the invention also encompass administration of the composition of the invention via instillation on the ocular surface. When the siRNA is administered directly to the eye, generally an amount of between about 0.01 mg and about 100 mg per eye per day, between about 0.08 mg and about 0.9 mg per eye per day, between about 0.08 mg and about 0.6 mg per eye per day, between about 0.08 mg and about 0.45 mg per eye per day, between about 0.08 mg and about 0.3 mg per eye per day, between about 0.08 mg and about 0.15 mg per eye per day, between about 0.15 mg and about 0.9 mg per eye per day, between about 0.15 mg and about 0.6 mg per eye per day, between about 0.15 mg and about 0.45 mg per eye per day, between about 0.15 mg and about 0.3 mg per eye per day, between about 0.3 mg and about 0.9 mg per eye per day, between about 0.3 mg and about 0.6 mg per eye per day, between about 0.3 and about 0.45 mg per eye per day, between about 0.45 mg and about 0.9 mg per eye per day, between about 0.45 mg and about 0.6 mg per eye per day, or between about 0.6 mg and about 0.9 mg per eye per day of siNA is administered.

In specific embodiments, the dose for ocular instillation of a composition comprising or consisting of an siNA of the invention, preferably SYL040012, is about 0.15 mg, 0.3 mg, 0.45 mg, 0.6 mg, or 0.9 mg per eye per day.

The invention also relates to a dispenser for dispensing a pharmaceutical dosage in liquid form, said dispenser comprising a container for holding a charge of said liquid and an orifice for dispensing a droplet of said liquid of predetermined size, wherein said liquid comprises between about 0.08 mg and about 0.9 mg of a siNA comprising an siNA of the invention and optionally one or more pharmaceutically acceptable diluents and optionally one or more excipients. In one embodiment, the siNA of the invention is selected from SEQ ID NOs. 2 or 3.

The invention also relates to a dispenser for dispensing a pharmaceutical dosage in liquid form, said dispenser comprising a container for holding a charge of said liquid and an orifice for dispensing a droplet of said liquid of predetermined size, wherein said liquid comprises between about 0.08 mg and about 0.9 mg of a an siNA of the invention in a solution comprising phosphate-buffered saline at a concentration of between about 2 mg/ml and about 22.5 mg/ml. In one embodiment, the siNA of the invention is selected from SEQ ID NOs. 2 or 3.

The invention also relates to a kit comprising:
(a) a dispenser for dispensing a pharmaceutical dosage in liquid form, said dispenser comprising a container for holding a charge of said liquid and an orifice for dispensing a droplet of said liquid of predetermined size; and
(b) written instructions specifying that between about 0.08 mg and about 0.9 mg of an siNA comprising an siNA of the invention in the form of one droplet is to be applied to each eye. In one embodiment, the siNA of the invention is selected from SEQ ID NOs 2 or 3.

The invention also relates to a kit comprising:

(a) a dispenser for dispensing a pharmaceutical dosage in liquid form, said dispenser comprising a container for holding a charge of said liquid and an orifice for dispensing a droplet of said liquid of predetermined size; and (b) written instructions specifying that between about 0.08 mg and about 0.9 mg of a nucleic acid of an siNA of the invention in a final concentration of between about 2 mg/ml and about 22.5 mg/ml in PBS in the form of one droplet is to be applied to each eye. In one embodiment, the siNA of the invention is selected from SEQ ID NOs. 2 or 3.

The invention also relates to the use of a short interfering nucleic acid molecule (siNA) comprising the nucleotide sequence of an siNA of the invention in the manufacture of a medicament for the treatment of an eye disorder characterized by increased intraocular pressure (IOP) wherein said siRNA is topically administered to the corneal surface of the eye of a patient in need thereof at a dose of between about 0.08 mg and about 0.9 mg. In one embodiment, the siNA of the invention is selected from SEQ ID NOs. 2 or 3.

The invention also relates to a short interfering nucleic acid molecule (siNA) comprising the nucleotide sequence of an siNA of the invention for use in the treatment of an eye disorder characterized by increased intraocular pressure (IOP) wherein said siRNA is topically administered to the corneal surface of the eye of a patient in need thereof at a dose of between about 0.08 mg and about 0.9 mg. In one embodiment, the siNA of the invention is selected from SEQ ID NOs. 2 or 3.

DETAILED DESCRIPTION OF THE INVENTION

The present invention relates to methods, compositions and dosages that decrease IOP of the eye. The compositions of the invention comprise short interfering nucleic acid molecules (siNA) that decrease expression of adrenergic receptor beta 2 (ADRB2) gene, which, as indicated previously, the expression product of which decreases production of aqueous humor within the anterior chamber of the eye. The compositions of the invention can be used in the preparation of a medicament for the treatment of an eye condition displaying increased IOP such as glaucoma. The methods of the invention comprise the administration to a patient in need thereof of an effective amount of one or more siNAs of the invention in an effective dosing regimen.

Design of siNAs siNAs of the invention are designed to modulate the activity by decreasing or inhibiting the expression of ADRB2, thus affecting IOP. In one embodiment, a decrease in or inhibition of the target gene expression decreases the production of intraocular fluid e.g. aqueous humor. GenBank accession number for ADRB2, the present target gene, is NM_000024 incorporated by reference.

As used herein "siNAs" of the invention refers to a double stranded oligonucleotide capable of mediating target mRNA cleavage via RNA interference. It is preferred to the term siRNA to avoid confusion, given that it is a common practice in the field to include modified non-canonical bases within the molecule structure, and on occasion a deoxyribonucleotide, including single-stranded thymidine overhangs at the ends of the double-stranded portion.

A gene is "targeted" by a siNA according to the invention when, for example, the siNA molecule selectively decreases or inhibits the expression of the gene. The phrase "selectively decrease or inhibit" as used herein encompasses siNAs that decrease expression of one gene as well those that decrease the expression of more than one gene. In cases where an siNA decreases expression of more than one gene, the gene that is targeted is decreased at least about two times, about three times, about four times, about five times, about ten times, about twenty five times, about fifty times, or about one hundred times as much as any other gene. Alternatively, a siNA targets a gene when the siNA hybridizes under stringent conditions to the gene transcript. siNAs can be tested either in vitro or in vivo for the ability to target a gene.

A short fragment of the target gene's mRNA sequence (e.g. 19-40 nucleotides in length) is chosen for the sequence of the siNA of the invention. In one embodiment the siNA is a siRNA. In preferred embodiments, the criteria for choosing a sequence fragment from the target gene mRNA to be a candidate siRNA molecule include 1) a sequence from the target gene mRNA that is at least 50-100 nucleotides from the 5' or 3' end of the native mRNA molecule, 2) a sequence from the target gene mRNA that has a G/C content of between 30% and 70%, most preferably around 50%, 3) a sequence from the target gene mRNA that does not contain repetitive sequences (e.g. AAA, CCC, GGG, UUU, AAAA, CCCC, GGGG, UUUU), 4) a sequence from the target gene mRNA that is accessible in the mRNA, and 5) a sequence from the target gene mRNA that is unique to the target gene. The sequence fragment from the target gene mRNA may meet one or more criteria identified above. In embodiments where a fragment of the target gene mRNA meets less than all of the criteria identified supra, the native sequence may be altered such that the siRNA conforms with more of the criteria than does the fragment of the target gene mRNA. In preferred embodiments, the siRNA has a G/C content below 60% and/or lacks repetitive sequences.

In one specific embodiment, the portion of the siNA that is complementary to the target region is perfectly complementary to the target region. In another specific embodiment, the portion of the siNA that is complementary to the target region is not perfectly complementary to the target region. siNA with insertions, deletions, and point mutations relative to the target sequence are also encompassed by the invention. Thus, sequence identity may be calculated by sequence comparison and alignment algorithms known in the art (see Gribskov and Devereux, Sequence Analysis Primer, Stockton Press 1991, and references cited therein) and calculating the percent difference between the nucleotide sequences by, for example, the Smith-Waterman algorithm as implemented in the BESTFIT software program using default parameters (e.g. University of Wisconsin Genetic Computing Group). Greater than 90%, 95%, or 99% sequence identity between the siNA and the portion of the target gene is preferred. Alternatively, the complementarity between the siNA and native RNA molecule may be defined functionally by hybridization. A siNA sequence of the invention is capable of hybridizing with a portion of the target gene transcript under stringent conditions (e.g. 400 mM NaCl, 40 mM PIPES pH 6.4, 1 mM EDTA, 50° C. or 70° C. hybridization for 12-16 hours; followed by washing). A siNA sequence of the invention can also be defined functionally by its ability to decrease or inhibit the expression of a target gene. The ability of a siNA to affect gene expression can be determined empirically either in vivo or in vitro.

In addition to siNAs which specifically target only one gene, degenerate siNA sequences may be used to target homologous regions of multiple genes. WO2005/045037 describes the design of siNA molecules to target such homologous sequences, for example by incorporating non-canonical base pairs, for example mismatches and/or wobble base pairs, that can provide additional target sequences. In instances where mismatches are identified, non-canonical base pairs (for example, mismatches and/or wobble bases) can be used to generate siNA molecules that target more than one gene sequence. In a non-limiting example, noncanonical base pairs such as UU and CC base pairs are used to generate siNA molecules that are capable of targeting sequences for differing targets that share sequence homology. As such, one advantage of using siNAs of the invention is that a single siNA can be designed to include a nucleic acid sequence that is complementary to the nucleotide sequence that is conserved between homologous genes. In this approach, a single siNA can be used to inhibit expression of more than one gene instead of using more than one siNA molecule to target different genes.

Preferred siNA molecules of the invention are double-stranded. In one embodiment, double stranded siNA molecules comprise blunt-ends. In another embodiment, double stranded siNA molecules comprise overhanging nucleotides (e.g. 1-5 nucleotide overhangs, preferably 2 nucleotide overhangs). In a specific embodiment, the overhanging nucleotides are 3' overhangs. In another specific embodiment, the overhanging nucleotides are 5' overhangs. Any type of nucleotide can be a part of the overhang. In one embodiment, the overhanging nucleotide or nucleotides are ribonucleic acids. In another embodiment, the overhanging nucleotide or nucleotides are deoxyribonucleic acids. In a preferred embodiment, the overhanging nucleotide or nucleotides are thymidine nucleotides. In another embodiment, the overhanging nucleotide or nucleotides are modified or non-classical nucleotides. The overhanging nucleotide or nucleotides may have non-classical internucleotide bonds (e.g. other than phosphodiester bond).

In preferred embodiments, siNA compositions of the invention are designed to target SEQ ID NO: 1 (CAUUGUGCAUGUGAUCCAG). Further embodiments refer to siNAs identified by SEQ ID NO 1, SEQ ID NO 2 (sense strand: CAUUGUGCAUGUGAUCCAG dT dT), SEQ ID NO 3 (sense strand: CAUUGUGCAUGUGAUCCAG), SEQ ID NO 4 (sense strand: CAUUGUGCAUGUGAUC-CAG), SEQ ID NO 5 (sense strand: CAUUGUGCAU-GUGAUCCAG dT dT-3') and SEQ ID NO 6 (sense strand: CAUUGUGCAUGUGAUCCAG dU dU). Full sequences of the double stranded molecules are shown in FIG. 5. In another embodiment, the preferred siNA according to the various aspects of the invention is SEQ ID NO: 2 (SYL040012). This preferred siNA SYL040012, is a 19 nt long unmodified double stranded RNA molecule with dinucleotide overhangs at the 3' ends comprising deoxythymidine bases, as depicted in FIG. 5.

Synthesis of siNAs siNAs designed by methods described above can be synthesized by any method known in the art. RNAs are preferably chemically synthesized using appropriately protected ribonucleoside phosphoramidites and a conventional DNA/RNA synthesizer. Additionally, siRNAs can be obtained from commercial RNA oligo synthesis suppliers, including, but not limited to, Proligo (Hamburg, Germany), Dharmacon Research (Lafayette, Colo., USA), Glen Research (Sterling, Va., USA), ChemGenes (Ashland, Mass., USA), and Cruachem (Glasgow, UK), Qiagen (Germany), Ambion (USA) and Invitrogen (Scotland). Alternatively, siNA molecules of the invention can be expressed in cells by transfecting the cells with vectors containing the reverse complement siNA sequence under the control of a promoter. Once expressed, the siNA can be isolated from the cell using techniques well known in the art.

In embodiments where the siRNA is a double-stranded RNA (dsRNA), an annealing step is necessary if single-stranded RNA molecules are obtained. Briefly, combine 30 ml of each RNA oligo 50 mM solution in 100 mM potassium acetate, 30 mM HEPES-KOH pH 7.4, 2 mM magnesium acetate. The solution is then incubated for 1 minute at 90° C., centrifuged for 15 seconds, and incubated for 1 hour at 37° C.

In embodiments where the siRNA is a short hairpin RNA (shRNA); the two strands of the siRNA molecule may be connected by a linker region (e.g., a nucleotide linker or a non-nucleotide linker).

Chemical Modification of siNAs

The siNAs of the invention may contain one or more modified nucleotides and/or non-phosphodiester linkages. Chemical modifications well known in the art are capable of increasing stability, availability, and/or cell uptake of the siNA. The skilled person will be aware of other types of chemical modification which may be incorporated into RNA molecules (see International Publications W0031070744 W02005/045037 or WO2008/104978 for an overview of types of modifications).

In one embodiment, modifications can be used to provide improved resistance to degradation or improved uptake. Examples of such modifications include phosphorothioate internucleotide linkages, 2'-O-methyl ribonucleotides (especially on the sense strand of a double stranded siRNA), 2'-deoxy-fluoro ribonucleotides, 2'-deoxy ribonucleotides, "universal base" nucleotides, 5-C-methyl nucleotides, and inverted deoxyabasic residue incorporation (see generally GB2406568).

In another embodiment, modifications can be used to enhance the stability of the siRNA or to increase targeting efficiency. Modifications include chemical cross linking between the two complementary strands of an siRNA, chemical modification of a 3' or 5' terminus of a strand of an siRNA, sugar modifications, nucleobase modifications and/or backbone modifications, 2'-fluoro modified ribonucleotides and 2'-deoxy ribonucleotides (see generally International Publication W02004/029212).

In another embodiment, modifications can be used to increase or decrease affinity for the complementary nucleotides in the target mRNA and/or in the complementary siNA strand (see generally International Publication W02005/044976). For example, an unmodified pyrimidine nucleotide can be substituted for a 2-thio, 5-alkynyl, 5-methyl, or 5-propynyl pyrimidine. Additionally, an unmodified purine can be substituted with a 7-deza, 7-alkyl, or 7-alkenyl purine.

In another embodiment, when the siNA is a double-stranded siRNA, the 3'-terminal nucleotide overhanging nucleotides are replaced by deoxyribonucleotides, preferably deoxythymidines, see for example Elbashir et al[33].

Demonstration of Therapeutic Utility

The compositions and methods of the invention are preferably tested in vitro, and then in vivo, for the desired therapeutic activity prior to use in humans. For example, in vitro assays which can be used to determine whether administration of a specific therapeutic protocol is indicated, include in vitro cell culture assays in which a candidate siNA is administered to cells (e.g., rabbit non-pigmented ciliary epithelium cells (NPE), human ciliary epithelium cells (OMDC), or human embryonic kidney cells (HEK293)) in vitro and the effect of such protocol upon the cells is observed, e.g., decreased or inhibited expression of the target gene.

Compounds for use in therapy can be tested in suitable animal model systems prior to testing in humans, including but not limited to in rabbits, rats, mice, chicken, cows, monkeys, hamsters, etc. For example, the New Zealand rabbit is the preferred standard in experimental platforms designed to study IOP. It is easy to handle and it has a big eye, similar in size to the human organ. In addition, present equipment to measure IOP is not suited to use in animals with small eyes such as mice or rats. Finally, rabbits have an IOP that can be reduced to 40% of its normal (or pre-drug) value using local commercial hypotensive medication. Thus, although it is possible to generate rabbit glaucoma models (for example, surgically blocking episclerotic veins or artificially occluding the trabecular meshwork), generally those in the field prefer models in which ocular structures remain intact.

Therapeutic Methods

The present invention encompasses methods for treating, preventing, or managing an eye disorder associated with increased IOP in a patient (e.g., a mammal, especially humans) comprising administering an effective amount of one or more siNAs of the invention. The present invention encompasses siNAs of the invention for use in treating, preventing, or managing an eye disorder associated with increased IOP in a patient (e.g., a mammal, especially humans) comprising administering an effective amount of one or more siNAs of the invention. In a specific embodiment, the disorder to be treated, prevented, or managed is glaucoma. Any type of glaucoma that is associated with IOP can be treated with the methods of the present invention including, but not limited to, Open Angle Glaucoma (e.g., Primary Open Angle Glaucoma, Pigmentary Glaucoma, and Exfoliative Glaucoma, Low Tension Glaucoma), Angle Closure Glaucoma (also known clinically as closed angle glaucoma, narrow angle glaucoma, pupillary block glaucoma, and ciliary block glaucoma) (e.g., Acute Angle Closure Glaucoma and Chronic Angle Closure Glaucoma), Aniridic Glaucoma, Congenital Glaucoma, Juvenile Glaucoma, Lens-Induced Glaucoma, Neovascular Glaucoma, Post-Traumatic Glaucoma, Steroid-Induced Glaucoma, Sturge-Weber Syndrome Glaucoma, and Uveitis-Induced Glaucoma.

Therapeutic treatments with siRNAs directed against specific target genes are expected to be beneficial over small molecule topical ocular drops by increasing the length of time that effect is observed, thereby allowing less frequent dosing and greater patient compliance.

In preferred embodiments, the siNAs used in the therapeutic methods of the invention decrease or inhibit the expression of genes that effect IOP, such as adrenergic receptor beta 2. In further preferred embodiments of the invention, the siNAs used in the therapeutic methods of the invention are targeted to SEQ ID NO: 1. In a specific preferred embodiment, the siNA is 21 to 30 nucleotides in length and comprises SEQ ID NO: 3. Specifically preferred is SYL040012, with SEQ ID NO: 2 having no modifications, i.e. no non canonical bases, and comprising dideoxythymidine overhangs on both 3' ends.

In preferred embodiments, the methods of the invention provide a sustained decrease in IOP that lasts for longer than 8, 10, 12, or 14 hours, more preferably for several days (e.g., 2 days, 3 days, 4 days, or 5 days), after the last administration of siNA. In such embodiments, the effect (i.e., decreased IOP) of administered siNAs of the invention is longer lasting than the duration of IOP decrease that typically results from administration of presently commercially available drugs (e.g., Xalatan, Trusopt, and Timoftol). The siNAs of the invention that provide sustained IOP decreasing action can be administered in a regimen such that IOP is continually decreased without daily administration of the siNA. In a specific embodiment, a treatment regimen can include consecutive cycles of administration (e.g., one dose of siNA given daily for four days) and non-administration (e.g., 3 or 4 days with no treatment given) while still eliciting a continual decrease in IOP.

In one embodiment, a single type of siNA is administered in the therapeutic methods of the invention. In another embodiment, a siNA of the invention is administered in combination with another siNA of the invention and/or with one or more other non-siNA therapeutic agents useful in the treatment, prevention or management of an eye disorder associated with increased IOP. The term "in combination with" is not limited to the administration of therapeutic agents at exactly the same time, but rather it is meant that the siNAs of the invention and the other agent are administered to a patient in a sequence and within a time interval such that the benefit of the combination is greater than the benefit if they were administered otherwise. For example, each therapeutic agent may be administered at the same time or sequentially in any order at different points in time; however, if not administered at the same time, they should be administered sufficiently close in time so as to provide the desired therapeutic effect. Each therapeutic agent can be administered separately, in any appropriate form and by any suitable route.

Dosage

As used herein, an "effective amount" refers to that amount of a siNA of the invention sufficient to treat or manage an eye disorder associated with increased IOP and, preferably, the amount sufficient to decrease IOP. For treatment of increased IOP in humans, it is preferred to reduce IOP so that IOP is between about 14 and 20 mm Hg. However, any reduction in IOP as compared to pretreatment IOP is advantageous, whether the compounds of the invention are delivered alone, or in combination with another suitable therapeutic (e.g., the invention contemplates a decrease in IOP greater that about 5%, about 10%, about 25%, about 30%, about 35%, about 40%, about 50%, or about 60% of pretreatment IOP). In some embodiments, the compounds of the invention can cause a decrease in IOP that is between about 1% and about 99%, between about 5% and about 90%, between about 10% and about 80%, between about 20% and about 50%, or between about 25% and about 45% of pretreatment IOP. Preferably, the decrease in IOP is between about 25% and about 30%. A therapeutically effective amount may also refer to the amount of an siNA sufficient to delay or minimize the onset of an eye disorder associated with increased IOP. A therapeutically effective amount may also refer to the amount of the therapeutic agent that provides a therapeutic benefit in the treatment or management of an eye disorder associated with elevated IOP. Further, a therapeutically effective amount with respect to an siNA of the invention means that amount of therapeutic agent alone, or in combination with other therapies, that provides a therapeutic benefit in the treatment or management of an eye disorder associated with increased IOP. Used in connection with an amount of an siRNA of the invention, the term can encompass an amount that improves overall therapy, reduces or avoids unwanted effects, or enhances the therapeutic efficacy of or synergizes with another therapeutic agent. Treatment with siNA alone or in combination should result in an IOP of about 14 and 20 mm Hg. However, any decrease in IOP as compared to pretreatment IOP is advantageous (e.g., a decrease in IOP greater that 5%, 10%, 25%, 30%, 35%, 40%, 50%, or 60% of pretreatment IOP).

A therapeutic benefit in the treatment or management of an eye disorder associated with increased IOP is the sustained decrease in IOP induced by the treatment. The more sustained the decrease is, the less likelihood there is of sudden sharp increases in IOP occurring when the next dose becomes due. This is considered a significant enhancement of the therapeutic efficacy. In some embodiments, treatment with siNA alone or in combination can result in a decrease in IOP sustained between about 2 days to about 7 days, between about 2 and about 6 days, and between about 2 days and about 4 days. In some preferred embodiment, the decrease is sustained between about 2 days and about 3 days, preferably during 3 days.

Consequently, in some embodiments administration of the compounds of the invention results in preventing, protecting against, or reducing the damage to the optic nerve caused by the reboot effect in IOP when the next dose becomes due in cases of patients' poor compliance with treatment schedules.

The effective amount and treatment regimen of a composition of the invention can be determined by standard research techniques. For example, the dosage of the composition which will be effective in the treatment, prevention or management of the disorder can be determined by administering the composition to an animal model such as, e.g., the animal models disclosed herein, e.g. the New Zealand white rabbit model, or known to those skilled in the art. In addition, in vitro assays may optionally be employed to help identify optimal dosage ranges. Alternatively, the dosage may be determined for an individual by titrating the dose until an effective level is reached.

Selection of the preferred effective amount to be used in dosages can be determined (e.g., via clinical trials) by a skilled artisan based upon the consideration of several factors which will be known to one of ordinary skill in the art. Such factors include the disorder to be treated or prevented, the symptoms involved, the patient's body mass, the patient's immune status and other factors known by the skilled artisan to reflect the accuracy of administered pharmaceutical compositions.

The precise dose to be employed in the formulation will also depend on the route of administration, and the seriousness of the disorder, and should be decided according to the judgment of the practitioner and each patient's circumstances.

When the siRNA featured herein is administered directly to the eye, the dosage is sufficient to inhibit expression of the target genes. In general, a suitable dose of siRNA will be in the range of about 0.01 mg and about 100 mg per eye per day, between about 0.08 mg and about 0.9 mg per eye per day, between about 0.08 mg and about 0.6 mg per eye per day, between about 0.08 mg and about 0.45 mg per eye per day, between about 0.08 mg and about 0.3 mg per eye per day, between about 0.08 mg and about 0.15 mg per eye per day, between about 0.15 mg and about 0.9 mg per eye per day, between about 0.15 mg and about 0.6 mg per eye per day, between about 0.15 mg and about 0.45 mg per eye per day, between about 0.15 mg and about 0.3 mg per eye per day, between about 0.3 mg and about 0.9 mg per eye per day, between about 0.3 mg and about 0.6 mg per eye per day, between about 0.3 and about 0.45 mg per eye per day, or between about 0.45 mg and about 0.9 mg per eye per day, between about 0.45 mg and about 0.6 mg per eye per day, or between about 0.6 mg and about 0.9 mg per eye per day of siNA is administered.

For example, the siRNA can be administered at about: 0.01 mg, 0.02 mg, 0.03 mg, 0.04 mg, 0.05 mg, 0.06 mg, 0.07 mg, 0.08 mg, 0.09 mg, 0.1 mg, 0.11 mg, 0.12 mg, 0.13 mg, 0.14 mg, 0.15 mg, 0.16 mg, 0.17 mg, 0.18 mg, 0.19 mg, 0.2 mg, 0.21 mg, 0.22 mg, 0.23 mg, 0.24 mg, 0.25 mg, 0.26 mg, 0.27 mg, 0.28 mg, 0.29 mg, 0.3 mg, 0.31 mg, 0.32 mg, 0.33 mg, 0.34 mg, 0.35 mg, 0.36 mg, 0.37 mg, 0.38 mg, 0.39 mg, 0.4 mg, 0.41 mg, 0.42 mg, 0.43 mg, 0.44 mg, 0.45 mg, 0.46 mg, 0.47 mg, 0.48 mg, 0.49 mg, 0.5 mg, 0.51 mg, 0.52 mg, 0.53 mg, 0.54 mg, 0.55 mg, 0.56 mg, 0.57 mg, 0.58 mg, 0.59 mg, 0.6 mg, 0.61 mg, 0.62 mg, 0.63 mg, 0.64 mg, 0.65 mg, 0.66 mg, 0.67 mg, 0.68 mg, 0.69 mg, 0.7 mg, 0.71 mg, 0.72 mg, 0.73 mg, 0.74 mg, 0.75 mg, 0.76 mg, 0.77 mg, 0.78 mg, 0.79 mg, 0.8 mg, 0.81 mg, 0.82 mg, 0.83 mg, 0.84 mg, 0.85 mg, 0.86 mg, 0.87 mg, 0.88 mg, 0.89 mg, 0.9 mg, 0.91 mg, 0.92 mg, 0.93 mg, 0.94 mg, 0.95 mg, 0.96 mg, 0.97 mg, 0.98 mg, 0.99 mg, or 1 mg, per eye per day.

In a preferred embodiment the siNA of the invention is formulated in a saline solution such as PBS. In a specifically preferred embodiment the siRNA of the invention is SYL040012 and is administered at the above defined doses. In some preferred embodiments, these doses may be administered once a day, twice a day, three times a day or four times a day, and the application to each eye is to take place daily, every other day, once a week, twice a week, three times a week, every other week, or once a month. In some embodiments the above doses may be administered at the same time each day or at different times each day. Given that pathologies characterized by increased IOP such as glaucoma are chronic in nature, in a preferred embodiment of the present invention the administration of the siNAs of the invention is also chronic. In certain embodiments, the siNA of the invention is administered regularly (e.g., daily, twice daily, every other day, etc.) over a period of at least 7 days, 14 days or 28 days. In alternative embodiments of the invention, where an increase in the patients' IOP is transitory the compositions of the invention shall be administered while the condition persists.

Formulations and Routes of Administration

The siNAs of the invention may be formulated into pharmaceutical compositions by any of the conventional techniques known in the art (see for example, Alfonso, G. et al., 1995, in: The Science and Practice of Pharmacy, Mack Publishing, Easton Pa., 19th ed.). Formulations comprising one or more siNAs for use in the methods of the invention may be in numerous forms, and may depend on the various factors specific for each patient (e.g., the type and severity of disorder, type of siNA administered, age, body weight, response, and the past medical history of the patient), the number and type of siNAs in the formulation, the form of the composition (e.g., in liquid, semi-liquid or solid form), the therapeutic regime (e.g. whether the therapeutic agent is administered over time once daily, several times a day or once every few days, and/or the route of administration).

In a preferred embodiment, the compositions of the invention are administered in the form of eye drops, delivered directly to the eye. The eye drops can be delivered in a volume of between about 10 µl and about 100 µl per drop, more preferably between about 20 µl and about 50 µl per drop, and most preferably between about 20 µl and about 33 µl per drop. In an additionally preferred embodiment the eyedrops are delivered in a volume of about 26.6 or about 40 µl. In a preferred embodiment the composition of the invention comprises SYL040012 in an acceptable solution such as PBS. In some preferred embodiments SYL040012 is administered once a day in eyedrops at a concentration of from about 0.25 mg/ml to about 25 mg/ml, preferably between 2 mg/ml to about 22.5 mg/ml. For example, SYL040012 is administered at a concentration of from about: 0.25 mg/ml, 0.5 mg/ml, 0.75 mg/ml, 1 mg/ml, 1.25 mg/ml, 1.5 mg/ml, 1.75 mg/ml, 2 mg/ml, 2.25 mg/ml, 2.5 mg/ml, 2.75 mg/ml, 3 mg/ml, 3.25 mg/ml, 3.5 mg/ml, 3.75 mg/ml, 4 mg/ml, 4.25 mg/ml, 4.5 mg/ml, 4.75 mg/ml, 5 mg/ml, 5.25 mg/ml, 5.50 mg/ml, 5.75 mg/ml, 6 mg/ml, 6.25 mg/ml, 6.5 mg/ml, 6.75 mg/ml, 7 mg/ml, 7.25 mg/ml, 7.5 mg/ml, 7.75 mg/ml, 8 mg/ml, 8.25 mg/ml, 8.5 mg/ml, 8.75 mg/ml, 9 mg/ml, 9.5 mg/ml, 9.75 mg/ml, 10 mg/ml, 10.25 mg/ml, 10.5 mg/ml, 10.75 mg/ml, 11 mg/ml, 11.25 mg/ml, 11.5 mg/ml, 11.75 mg/ml, 12 mg/ml, 12.25 mg/ml, 12.5 mg/ml, 12.75 mg/ml, 13 mg/ml, 13.25 mg/ml, 13.5 mg/ml, 13.75 mg/ml, 14 mg/ml, 14.25 mg/ml, 14.5 mg/ml, 14.75 mg/ml, 15 mg/ml, 15.25 mg/ml, 15.5 mg/ml, 15.75 mg/ml, 16 mg/ml, 16.25 mg/ml, 16.5 mg/ml, 16.75 mg/ml, 17 mg/ml, 17.25 mg/ml, 17.5 mg/ml, 17.75 mg/ml, 18 mg/ml, 18.25 mg/ml, 18.5 mg/ml, 18.75 mg/ml, 19 mg/ml, 19.25 mg/ml, 19.5 mg/ml, 19.75 mg/ml, 20 mg/ml, 20.25 mg/ml, 20.5 mg/ml, 20.75 mg/ml, 21 mg/ml, 21.25 mg/ml, 21.5 mg/ml, 21.75 mg/ml, 22 mg/ml, 22.25 mg/ml, 22.5 mg/ml, 22.75 mg/ml, 23 mg/ml, 23.25 mg/ml, 23.5 mg/ml, 23.75 mg/ml, 24 mg/ml, 24.25 mg/ml, 24.5 mg/ml, 24.75 mg/ml, or 25 mg/ml.

These compositions can take the form of aqueous and non-aqueous solutions, suspensions, emulsions, microemulsions, aqueous and non-aqueous gels, creams, tablets, pills, capsules, powders, sustained-release formulations and the like. The siNAs of the invention can also be encapsulated in a delivery agent (including, but not limited to, liposomes, microspheres, microparticles, nanospheres, nanoparticles, biodegradable polymers, hydrogels, cyclodextrins poly (lactic-co-glycolic) acid (PLGA)) or complexed with polyethyleneimine and derivatives thereof (such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives). The preferred compositions of the invention are aqueous solutions, specifically preferred are saline solutions such as PBS, with a pH range of about 7.0 to about 7.4 preferably with a pH of 7.2±0.5.

Pharmaceutical carriers, vehicles, excipients, or diluents may be included in the compositions of the invention including, but not limited to, water, saline solutions, preferably buffered saline solutions, oils (e.g., petroleum, animal, vegetable or synthetic oils), starch, glucose, lactose, sucrose, gelatin, malt, rice, flour, chalk, silica gel, sodium stearate, glycerol monostearate, talc, sodium chloride, dried skimmed milk, glycerol, propylene, glycol, ethanol, biopolymers (e.g., carbopol, hialuronic acid, polyacrylic acid, etc.), dextrose, permeation enhancers (e.g., fatty acids, fatty acid esters, fatty alcohols and amino acids), and hydrophilic polymers (e.g., polycarbophil and polyvinylpyrrolidone) and the like. The composition, if desired, can also contain minor amounts of wetting or emulsifying agents, or pH buffering agents.

Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

In preferred embodiments, the compositions of the invention are formulated in a solution, preferably a buffered saline solution such as PBS, or a gel for topical administration to the eye, such as, for example, in the form of eye drops. In such embodiments, the formulations may be cationic emulsions and/or contain biopolymers including, but not limited to, poly(lactide-co-glycolide), carbopol, hialuronic acid and polyacrylic acid.

In a specific preferred embodiment, the compositions of the invention are formulated in a solution such as phosphate-buffered saline (PBS), which may optionally also comprise one or more pharmaceutically acceptable diluents and or excipients such as benzalkonium chloride, which will allow ocular instillation on the corneal surface in the form of an eyedrop preferably of between about 30 and about 40 In such preferred embodiments the dose administered is between about 0.08 mg and about 0.9 mg per eye per day, preferably administered once a day. For example, the dose administered is 0.08 mg, 0.15 mg, 0.3 mg, 0.45 mg, 0.6 mg, or 0.9 mg per eye per day.

The siNAs of the present invention can also be formulated in combination with other therapeutic compounds that decrease IOP (e.g., commercially available drugs).

Kits

The siNA compounds of the invention can also be provided in kits that comprise a dispenser with an orifice for dispensing specific dosages of the siNA compound in a droplet of predetermined volume. In a preferred embodiment the siNA compounds of the invention are siNAs targeted against SEQ ID NO: 1. In a further preferred embodiment the dispensers within the kit of the invention provide a composition comprising or consisting of as the sole active ingredient SYL040012. In another embodiment the kit can comprise a collection of single use dispenser, for example for use during one month, in this specific case, the case would contain 30 single use dispensers. The droplet can range from about 20 µl to about 100 µl in volume. The dispenser can be a single use dispenser and comprise between about 1 mg and about 2 mg of the siNA compounds of the invention, and optionally also comprise one or more pharmaceutically acceptable diluents, and optionally one or more excipients. The composition contained in the dispenser can comprise a concentration of between about 0.25 mg/ml to about 25 mg/ml of the siNA compound of the invention. For example, the concentration is 0.25 mg/ml, 2 mg/ml, 3.75 mg/ml, 7.5 mg/ml, 11.25 mg/ml, 15 mg/ml, or 22.5 mg/ml. Alternatively, the dispenser can be designed to be used for one month or more and the volumes contained will increase accordingly to provide the equivalent number of doses. Preferably, the kits of the invention can also comprise instructions specifying that a dosage of the siNA compound of between about 2 mg to about 22.5 mg in 1 droplet is to be applied to each eye. The instructions can further specify that the droplets are applied to each eye once a day, twice a day, three times a day, or four times a day, and that the application to each eye is to take place daily, every other day, once a week, twice a week, three times a week, every other week, or once a month.

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Modifications and variations of the present invention are possible in light of the above teachings.

EXAMPLES

Example 1: SYL040012 in Humans

Subjects

Thirty healthy volunteers who had an IOP below 21 mmHg, Snellen visual acuity of 20/25 or better and who were at least 18 years of age were recruited. All subjects completed the study according to the protocol. A comprehensive physical examination and an ocular examination were performed before admittance into the study to assure the suitability of the subjects for participation in the study.

Study Design

A single-center, parallel, controlled, open-label phase I clinical study was designed to evaluate safety, tolerability, and bioavailability of SYL040012 administered as eye drops. An additional aim of the study was to determine the effect of different doses of SYL040012 on IOP. In all cases, the drug was instilled in one randomly chosen eye only; the fellow eye remained untreated and served as a control for ocular tolerance and safety. Both eyes were monitored in a blinded fashion.

Treatment Schedule

To minimize the risk of adverse effects and in accordance with the Guidelines on Strategies to Identify and Mitigate Risks for First-in-Human Clinical Trials with Investigational Medicinal Products (EMEA/CHMP/SWP/28367/07), the intervention phase was divided into two intervals. Interval 1 began with instillation of a single dose of SYL040012 to one subject who was observed for 72 hours. Tolerability was assessed at 24, 48, and 72 hours after instillation; when the tolerability criterion was met 72 hours after instillation, the next subject was dosed. The same procedure was followed for each new subject until six subjects had been administered. Good tolerance and thus the possibility of including the next volunteer was defined as an absence of grade 3 or higher toxicity on the Common Terminology Criteria for Adverse Events v3.0 scale.14 Safety and tolerability were assessed before interval 2 began.

During interval 2 SYL040012 was administered in daily instillations over 7 consecutive days. Two doses were assayed in this interval, each of which was administered to 12 subjects. For safety reasons, an initial group of three subjects received the low dose (600 µg) of SYL040012; when the tolerability criterion previously described was met, the remaining subjects assigned to this dose were administered. The same procedure was performed for the high dose (900 µg).

All subjects were treated in the Clinical Investigation Unit of the hospital, which guaranteed protocol compliance.

IOP Measurements

During interval 1, IOP was measured 1, 2, 4, 48, and 72 hours after instillation using Goldmann tonometry with the subjects sitting. During interval 2, the IOP curves were determined before the first instillation (screening) and after 4 days of treatment. In both cases, IOP was measured at 9:00, 12:00, 15:00, 18:00, and 21:00 hours. IOP was also measured every time ocular tolerance was assessed during intervals 1 and 2, 1 hour before and after instillation. Measurements performed outside of an IOP curve were taken in the morning between 9:00 and 12:00.

Statistical Analysis

Ocular and conjunctival local tolerance after SYL040012 treatment was assessed by analyzing occurrence and frequency of ocular adverse effects 72 hours after instillation for interval 1 and 24 hours after the last instillation during interval 2. Comparisons were made between eyes (administered vs. non-administered) using the chi-squared test.

Analysis of single daily IOP values after one instillation was performed by comparing values obtained after SYL040012 instillation to the basal value at screening Statistical significance was assessed by paired Student's t test. The effect of SYL040012 on IOP during interval 2 was assessed by comparing the IOP curve obtained at day 4 to the one obtained at screening. Statistical significance was assessed by repeated measures two-way analysis of variance (ANOVA), using treatment and time of day as variables and IOP as the repeated measure followed by a Bonferroni post-hoc test to assess the significance at each time point. Other parameters (clinical analysis, visual acuity, symptom duration) were analyzed using paired Student's t tests or Wilcoxon test depending on compliance of the conditions required for using each of these statistical tests. $P<0.05$ was considered significant.

TABLE 1

Design of the clinical trial.

| Dose regime | Number of subjects | Doses | Sites | Outcomes |
|---|---|---|---|---|
| 7 repeated doses. Only one eye was treated. | 30 | 7 (one per day) | 2 sites: Ophthalmology Department at Clínica Universidad de Navarra Ophthalmology Service at Hospital Universitario Ramón y Cajal de Madrid | Primary endpoint: Tolerance in the ocular surface (cornea and conjunctiva) 24 h after the last administration. Secondary endpoints: Local tolerance after each study dose and systemic tolerance. Treatment repercussion on the ocular fundus or on visual acuity. Pharmacokinetics. Effects on IOP. |

Results: Effect of SYL040012 on IOP

No significant differences in IOP were seen between the values obtained at screening and those obtained following a single instillation of SYL040012. During interval 2, administration of SYL040012 on a repeated dose schedule over a period of 7 days reduced TOP values in 15 out of 24 healthy subjects regardless of the dose used. The 600 µg dose of SYL040012 caused an overall statistically significant decrease in IOP after 4 days of administration; the post hoc data analysis showed a significant effect of SYL040012 on the measurements obtained at 15:00 hours (FIG. 1A). Five volunteers who received this dose showed a mean reduction in IOP values exceeding 20% on day 4 compared to values at screening. We performed a separate analysis in this subgroup and found an overall statistically significant effect on IOP; the post hoc analysis revealed that the differences were statistically significant at all time-points studied (FIG. 1B). It is noteworthy that the basal IOP value in these five subjects was higher than the basal IOP values in other subjects (16.2±2.9 mmHg vs. 14.9±2.8 mmHg, respectively). This increased responsiveness with higher IOP values has been reported for other antiglaucoma drugs[34].

Example 2: Treatment of Ocular Hypertension or Open-Angle Glaucoma in Adults: A Double-Blind, Placebo Controlled, Multiple-Dose Efficacy Phase IIa Trial Patients A total of 80 male and female subjects in good or fair general health as assessed by the investigator, aged ≥18 years, with a previous history or newly diagnosed elevated IOP (≥21 mmHg) with or without open-angle glaucoma in both eyes are recruited. To be included in this study they must have a normal result, or result typical for open-angle glaucoma of the following assessments in both eyes:
- Visual field 24-2 or equivalent (24-2 Humphrey visual field SITA test, about 5 minutes per eye).
- Optical coherence tomography (OCT).
- Best corrected visual acuity ≥0.5 (20/40) on the Snellen chart, or ≤0.3 log MAR.
- Schirmer test (lacrimation).
- Funduscopy.

The main objective of this trial is to determine tolerability on the ocular surface (cornea and conjunctiva) and effect on intraocular pressure after a daily dose of SYL040012 during 14 days of treatment.

Secondary objectives include assessment of local tolerability after each dose, systemic tolerability (effect on laboratory parameters, physical examination, vital signs and electrocardiogram), and changes (if any) of the ocular fundus or visual acuity possibly related to the investigational product.

Baseline Period

Up to 30 days before the first administration of the investigational product subjects are enrolled for eligibility to participate in the Treatment Period of the clinical trial. If an anti-glaucoma medication requires washout, this period may be longer. Temporary prescription of anti-glaucoma medication requiring a short wash-out is allowed. If at the beginning of the baseline period the patient is on an anti-glaucoma medication with several weeks wash-out, the investigator may prescribe another anti-glaucoma medication with a short wash-out time in order to avoid the eyes being without IOP-lowering medication for several weeks.

Treatment Period

On Day 1 subjects are randomised to 80 μg SYL040012, 300 μg SYL040012, 900 μl SYL040012 or placebo in a ratio of 1:1:1:1 to be administered in eyedrops.

Subjects return each day (including bank holidays and weekends) to the site for investigational product administration and assessments. Subjects receive 1 dose of the investigational product once daily in both eyes for 14 days.

Follow-Up Visit

The final assessment will be done at the follow-up visit which takes place 4 to 7 days after the last investigational product administration (from 96 hours after the last administration [4 days]+3 days).

To determine the effect of SYL040012 on patients' IOP, a 24-hour curve of IOP measurements is obtained with a Goldmann tonometer the day before beginning treatment, and on day 14. Time points are adjusted to a classical timetable for IOP curve measurements (09:00, 12:00, 15:00 and 18:00 and at 9:00 next day). Furthermore single IOP measurements are performed on day 1, 7 and 15, and also during the follow up visit which takes place between 4 and 7 days after receiving the last administration.

TABLE 2

Design of the clinical trial. Medical condition: Subjects with ocular hypertension or open-angle glaucoma.

| Dose regime | Number of subjects | Doses | Sites | Outcomes |
|---|---|---|---|---|
| 14 repeated doses of 80; 300 or 900 μg/eye/day SYL040012 or placebo. Both eyes were treated | 124 enrolled 89 randomized 80 completed | 14 (one per day) | 3 countries: Spain, Germany and Estonia. 11 sites | Primary endpoint: Tolerability to the ocular surface (cornea and conjunctiva) 24 h after the last administration and the effect on intraocular pressure (IOP) after 14 days of treatment. Secondary endpoints: Local tolerance after each study dose and systemic tolerance. Treatment repercussion on the ocular fundus or on visual acuity. Pharmacokinetics. Effects on IOP. |

Results

Tolerance to the Ocular Surface

The treatment was well tolerated at the ocular surface at all doses (80 μg SYL040012, 300 μg SYL040012, 900 μg SYL040012) 24 h after the last administration; thus the primary endpoint of the study was met. No drug-related serious adverse events were observed throughout the treatment.

Effect on IOP

Figure 2:
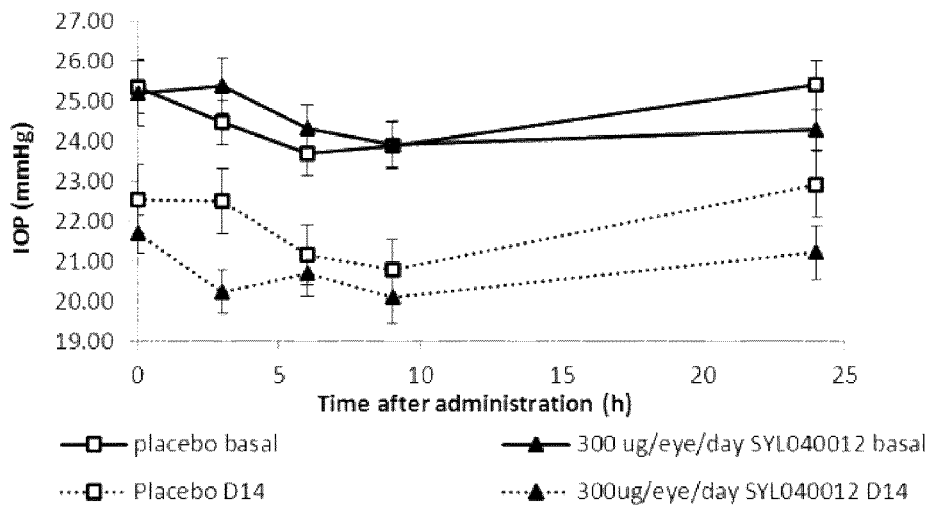
FIG. 2: IOP curve prior to initiation of treatment (basal) and in response to 300 μg/eye/day SYL040012. IOP evolution in subjects treated with repeated doses of either 300 μg/eye/day SYL040012 or placebo over a period of 14 days. Data represent means±S.E.M of the eye with highest basal mean IOP of 22 patients for placebo and 19 patients for SYL040012.

Administration of SYL040012 on a repeated dose schedule over a period of 14 days at the dose of 300 μg/eye/day caused a statistically significant reduction in IOP compared to baseline and to placebo (FIG. 2). Reductions in IOP in response to the dose of 300 μg/eye/day at each time point studied were −3.51 mmHg at 9:00; −5.12 mmHg at 12:00; −3.62 mmHg at 15:00; −3.82 mmHg at 18:00 and −4.17 mmHg at 21:00. It should be noted that the first measurement of each day was performed prior to administration of the investigational drug; thus reduction in IOP was maintained 24 h after administration indicating that the effect of the IOP lowering drug is long-lasting.

Figure 3:
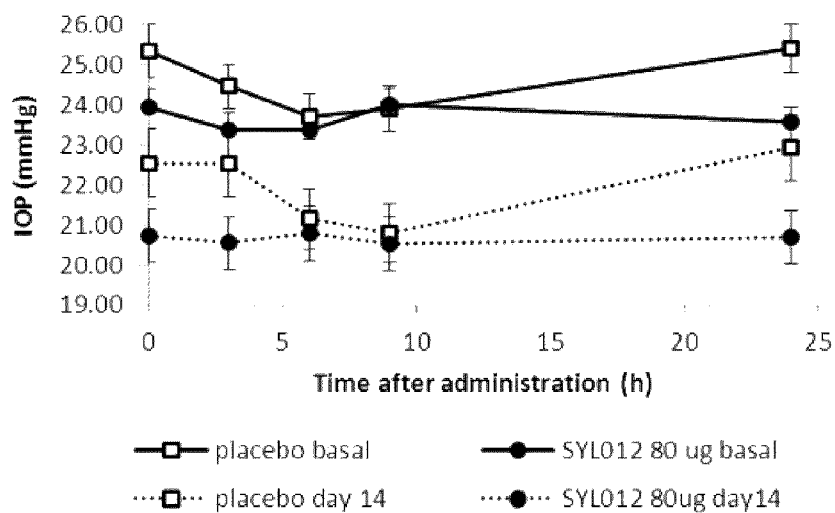
FIG. 3: IOP curve prior to initiation of treatment (basal) and in response to 80 μg/eye/day SYL040012. IOP evolution in subjects treated with repeated doses of either 80 μg/eye/day SYL040012 or placebo over a period of 14 days. Data represent means±S.E.M of the eye with highest basal mean IOP of 22 patients for placebo and 18 patients for SYL040012.
Figure 4:
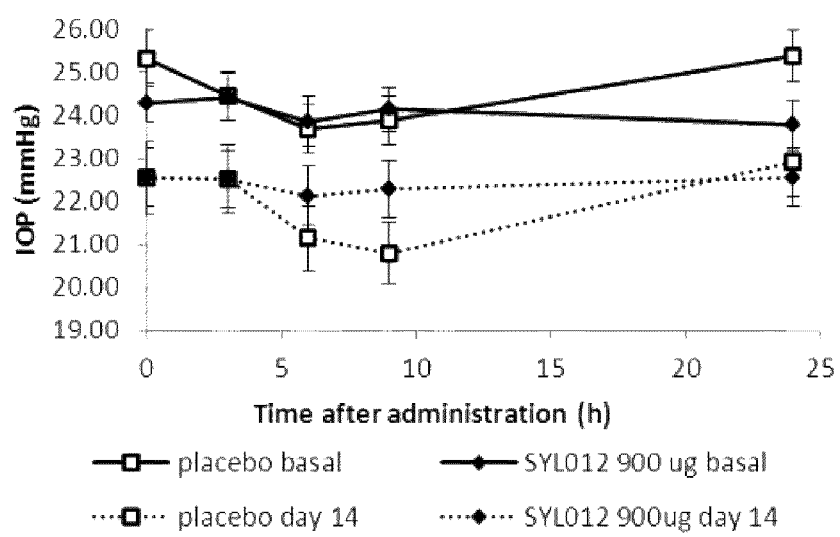
FIG. 4: IOP curve prior to initiation of treatment (basal) and in response to 900 μg/eye/day SYL040012. IOP evolution in subjects treated with repeated doses of either 900 μg/eye/day.

SYL040012 at the dose of 80 μg/eye/day reduced IOP compared to the baseline curve and to placebo, this effect was however only statistically significant when compared to baseline values and not when compared to placebo (FIG. 3). Reductions in IOP in response to the dose of 80 μg/eye/day at each time point studied were −3.20 mmHg at 9:00; −2.84 mmHg at 12:00; −2.60 mmHg at 15:00; −3.47 mmHg at 18:00 and −2.87 mmHg at 21:00.

The dose of 900 μg/eye/day showed a reduction in IOP when compared to basal values but the reduction in IOP was lower than the one observed in response to placebo (FIG. 3). Reductions in IOP in response to the dose of 900 μg/eye/day at each time point studied were: −1.62 mmHg at 9:00; −1.79 mmHg at 12:00; −1.47 mmHg at 15:00; −1.66 mmHg at 18:00 and −1.18 mmHg at 21:00.

SYL040012 or placebo over a period of 14 days. Data represent means±S.E.M of the eye with highest basal mean IOP of 22 patients for placebo and 20 patients for SYL040012.

TABLE 3

Percentage of patients showing a mean IOP below 21 mmHg at the end of treatment, in one eye or in both eyes.

| Treatment | Placebo | SYL040012 (μg/eye/day) | | |
|---|---|---|---|---|
| | | 80 | 300 | 900 |
| One eye <21 mmHg | 65.20% | 80.00% | 84.20% | 64.00% |
| Both eyes <21 mmHg | 43.50% | 65.00% | 68.40% | 44.00% |

Systemic Tolerance

The compound was very well tolerated with only a 14.6% of the patients reporting an adverse event; most of these events (80%) were of mild intensity. The most frequent adverse event was headache which was more frequent in the placebo treated group than in the SYL040012 groups. The only severe adverse event registered throughout the clinical trial was hyponatremia in one patient treated with SYL040012 at the dose of 300 μg/eye/day; this event was not considered to be related to the investigational product.

There were no significant or clinically relevant changes in the medical examination or in the laboratory tests. It should be noted that no alterations related to systemic inhibition of ADRB2 were observed.

Conclusion

The three doses of SYL040012 eye drops analyzed in the trial (80 μg SYL040012, 300 μg SYL040012, 900 μg SYL040012) were well-tolerated both locally (cornea and conjunctiva) and systemically, and they reduced intraocular pressure. The 300 μg dose of SYL040012 was found to produce a statistically significant reduction in intraocular pressure with respect to the placebo and to baseline IOP.

Example 3: SYL04012 Identification and Concentration Determination in Plasma Samples after its Ocular Topical Administration. Pharmacokinetics of SYL040012

Patients

A total of 24 male and female healthy volunteers were recruited to participate in the study: aged between 18 and 35 years, both inclusive. They were no smokers and had BMI between 18.5 and 30 kg/m². In order to be included in the study, their eye tests must result normal in both eyes.

Funduscopy

The main objective of this trial was to determine the following pharmacokinetic parameters:

AUC0-t (area under the curve of plasma to the last extraction at time t);

Cmax (maximum concentration).

Secondary objectives included determination of the following pharmacokinetic parameters:

tmax=time to reach Cmax,

AUC0-infinity=area under the plasma concentration curve from time zero extrapolated to infinity and from time t.

t½=terminal half-life.

R=accumulation after multiple doses.

Also, secondary objectives included the assessment of local and systemic tolerability after each dose.

Study Design

A single-center, parallel, random, double-blind study was designed to evaluate pharmacokinetics of SYL040012 administered as eyedrops.

Treatment Period

On Day 1 subjects were randomised to 80 μg SYL040012, 300 μg SYL040012, or placebo in a ratio of 1:1:1:1 to be administered in eyedrops.

Subjects return each day (including bank holidays and weekends) to the site for investigational product administration and assessments. Subjects receive 1 dose of the investigational product once daily in both eyes for 7 days.

Example 4: Treatment of Ocular Hypertension or Open-Angle Glaucoma in Adults: A Blind-Assessed, Active Controlled Phase IIb of SYL040012

Design:

The study was conducted in a total of approximately 17 centers in at least Spain, USA, Estonia and Germany. The duration of the study was 28 days, and it was a parallel, randomized, blind-assessed and active-controlled phase IIb study.

The disease or disorder under study was elevated IOP in subjects with ocular hypertension or open-angle glaucoma. The sample size in this study included a total of 180 randomized patients (36 per arm), with a sample size of 36 subjects per group (n=36/group).

The medicinal product tested was SYL040012 to be administered once daily in eyedrops in each eye over a period of 28 days (at doses of 150 μg SYL040012, 300 μg SYL040012, 450 μg SYL040012, and 600 μg SYL040012). As a control, an ophthalmic solution for ocular administration of Timolol maleate 0.5%, was administrated twice a day in each eye over a period of 28 days.

Patients

A total of 180 male and female subjects in good or fair general health as assessed by the investigator, aged ≥18 years, with a diagnosis of open-angle glaucoma or ocular hypertension in both eyes were recruited.

To be included in this study they must have been unmedicated (post-washout) and with an IOP≥23 mm Hg as the mean value of all the assessments performed at 09:00, 12:00, and 15:00 hours at baseline, in both eyes. In addition they must have a corrected visual acuity in each eye+1.0 log MAR or better by ETDRS in each eye (equivalent to 20/200).

Funduscopy

The main objective of this trial was to determine the efficacy of the treatment, the primary efficacy variable was the absolute change in mean diurnal IOP after 28 days of treatment (D28) vs. baseline (D0). The mean diurnal IOP was assessed as the mean value of the assessments at 09:00, 12:00 and 15:00, both at baseline and after 28 days.

Secondary objectives include assessment of secondary efficacy variables such as changes in the mean diurnal IOP value after 14 days of treatment (D14) vs baseline, assessed as the mean value of the assessments performed at 09:00, 12:00 and 15:00, both at baseline and after 14 days. The comparison in the mean diurnal IOP change vs. the active control (Timolol) after 14 and 28 days was also done. Also the assessment of safety variables such as local tolerability (comparison after 28 days of treatment vs. baseline or screening, based on where the last pre-treatment value was assessed):

VAS (Visual analogic scale) of local tolerability in case of symptoms
Visual acuity
Biomicroscopy
Pachymetry
Ophthalmoscopy
Systemic tolerability
   Physical examination
   Vital signs
   Laboratory analyses (hematology, biochemistry and urinalysis)
   12-lead ECG
Recording of adverse events (AEs).

REFERENCES CITED IN THE TEXT

1. Quigley H. Glaucoma. *Lancet* 2011; 377:1367-1377.
2. Weinreb R N, Khaw P T. Primary open-angle glaucoma. *Lancet* 2004; 363:1711-1720.
3. Glaucoma is the second leading cause of blindness globally. *Bulletin of the World Health Organization* 2004; 82:811-890.
4. Varma R, Lee P P, Goldberg I, Kotak S. An assessment of the health and economic burdens of glaucoma. *Am J Ophthalmol* 152:515-522.
5. Khaw P T, Shah P, Elkington A R. Glaucoma—1: diagnosis. *BMJ* 2004; 328:97-99.
6. Caprioli J, Varma R. Intraocular pressure: modulation as treatment for glaucoma. *Am J Ophthalmol* 152:340-344 e342.
7. Heijl A, Leske M C, Bengtsson B, Hyman L, Hussein M. Reduction of intraocular pressure and glaucoma progression: results from the Early Manifest Glaucoma Trial. *Arch Ophthalmol* 2002; 120:1268-1279.
8. Khaw P T, Shah P, Elkington A R. Glaucoma—2: treatment. *BMJ* 2004; 328:156-158.
9. Han J A, Frishman W H, Wu Sun S, Palmiero P M, Petrillo R. Cardiovascular and respiratory considerations with pharmacotherapy of glaucoma and ocular hypertension. *Cardiol Rev* 2008; 16:95-108.
10. Alm A, Camras C B, Watson P G. Phase III latanoprost studies in Scandinavia, the United Kingdom and the United States. *Surv Ophthalmol* 1997; 41 Suppl 2:S105-110.
11. Servat J J, Bernardino C R. Effects of common topical antiglaucoma medications on the ocular surface, eyelids and periorbital tissue. *Drugs Aging* 28:267-282.
12. De Natale R, Le Pen C, Berdeaux G. Efficiency of glaucoma drug regulation in 5 European countries: a 1995-2006 longitudinal prescription analysis. *J Glaucoma* 20:234-239.
13. Kass M A, Heuer D K, Higginbotham E J, et al. The Ocular Hypertension Treatment Study: a randomized trial determines that topical ocular hypotensive medication delays or prevents the onset of primary open-angle glaucoma. *Arch Ophthalmol* 2002; 120:701-713; discussion 829-730.
14. Singh K, Shrivastava A. Medical management of glaucoma: principles and practice. *Indian J Ophthalmol*; 59 Suppl:S88-92.
15. Gupta S K, Agarwal R, Galpalli N D, et al. Comparative efficacy of pilocarpine, timolol and latanoprost in experimental models of glaucoma. *Methods Find Exp Clin Pharmacol* 2007; 29(10):665-71.
16. Servat J J, Bernardino C R. Effects of common topical antiglaucoma medications on the ocular surface, eyelids and periorbital tissue. *Drugs Aging*; 28(4):267-82.
17. Han J A, Frishman W H, Wu Sun S, Palmiero P M, Petrillo R. Cardiovascular and respiratory considerations with pharmacotherapy of glaucoma and ocular hypertension. *Cardiol Rev* 2008; 16:95-108.
18. Nieminen T, Lehtimaki T, Maenpaa J, Ropo A, Uusitalo H, Kahonen M. Ophthalmic timolol: plasma concentration and systemic cardiopulmonary effects. *Scand J Clin Lab Invest* 2007; 67:237-245.
19. Zimmerman T J. Topical ophthalmic beta blockers: a comparative review. *J Ocul Pharmacol* 1993; 9:373-384.
20. Wax M B, Molinoff P B. Distribution and properties of beta-adrenergic receptors in human iris-ciliary body. *Invest Ophthalmol Vis Sci* 1987; 28:420-430.
21. Elena P P, Denis P, Kosina-Boix M, Saraux H, Lapalus P. Beta adrenergic binding sites in the human eye: an autoradiographic study. *J Ocul Pharmacol* 1990; 6:143-149.
22. Elena P P, Kosina-Boix M, Moulin G, Lapalus P. Autoradiographic localization of beta-adrenergic receptors in rabbit eye. *Invest Ophthalmol Vis Sci* 1987; 28:1436-1441.
23. Trope G E, Clark B. Beta adrenergic receptors in pigmented ciliary processes. *Br J Ophthalmol* 1982; 66:788-792.
24. Lu P Y, Xie F, Woodle M C. In vivo application of RNA interference: from functional genomics to therapeutics. *Adv Genet* 2005; 54:117-142.
25. Lopez-Fraga M, Martinez T, Jimenez A. RNA interference technologies and therapeutics: from basic research to products. *BioDrugs* 2009; 23:305-332.
26. Behlke M A. Progress towards in vivo use of siRNAs. *Mol Ther* 2006; 13(4):644-70.
27. Lu S, Cullen B R. Adenovirus VA1 noncoding RNA can inhibit small interfering RNA and MicroRNA biogenesis. *J Virol* 2004; 78(23):12868-76.
28. Miller V M, Gouvion C M, Davidson B L, Paulson H L. Targeting Alzheimer's disease genes with RNA interference: an efficient strategy for silencing mutant alleles. *Nucleic Acids Res* 2004; 32(2):661-8.
29. Nguyen Q D, Schachar R A, Nduaka C I, et al. Phase 1 dose-escalation study of a siRNA targeting the RTP801 gene in age-related macular degeneration patients. *Eye* (Lond) 2012.
30. DeVincenzo J, Lambkin-Williams R, Wilkinson T, et al. A randomized, double-blind, placebo-controlled study of an RNAi-based therapy directed against respiratory syncytial virus. Proc Natl Acad Sci USA 2010; 107(19):8800-5.
31. Behlke M A. Progress towards in vivo use of siRNAs. *Mol Ther* 2006; 13:644-670.
32. Campochiaro P A. Potential applications for RNAi to probe pathogenesis and develop new treatments for ocular disorders. *Gene Ther* 2006; 13:559-562.
33. Elbashir S M, Lendeckel W, Tuschl T. RNA interference is mediated by 21- and 22-nucleotide RNAs. *Genes Dev* 2001; 15:188-200.
34. Yoshida K, Tanihara H, Hiroi K, Honda Y. Prognostic factors for hypotensive effects of isopropyl unoprostone in eyes with primary open-angle glaucoma. Jpn J Ophthalmol 1998; 42(5):417-23.

The invention claimed is:

1. A method of treating an eye disorder characterized by increased intraocular pressure (IOP), said method comprising topically administering to the corneal surface of the eye of a human patient in need thereof a composition comprising between 0.08 mg and 0.29 mg per eye per day of SYL040012.

2. The method of claim 1, wherein the composition is administered once per day.

3. The method of claim 1, wherein the composition is delivered in a volume of between about 25 µl and about 40 µl.

4. The method of claim 1, wherein the composition is delivered to the eye with an eyedropper.

5. The method of claim 1, wherein the TOP of the patient is reduced by between about 25% and about 30% following administration of the composition to the patient compared with the TOP of the patient prior to the administration of the composition to the patient.

6. The method of claim 1, wherein the administration of SYL040012 provides a sustained decrease in TOP that lasts for longer than 24 hours after administration of SYL040012.

7. The method of claim 1, wherein the decrease in TOP is present for at least 8 hours.

8. The method of claim 1, wherein decreased TOP persists for at least 2 days.

9. The method of claim 1, wherein the eye disorder is selected from the group consisting of open angle glaucoma, angle closure glaucoma, and congenital glaucoma.

10. The method of claim 1, wherein SYL040012 is administered to the eye in a dose of 0.15 mg to 0.29 mg per eye per day.

11. The method of claim 1, wherein SYL040012 is administered to the eye in a dose of 0.15 mg per eye per day.

* * * * *